(12) United States Patent
Mann et al.

(10) Patent No.: US 11,415,579 B2
(45) Date of Patent: Aug. 16, 2022

(54) ASSAY FOR MEASURING A RATE OF REACTION BETWEEN A TARGET AND A LIGAND CANDIDATE

(71) Applicant: Imperial College Innovations Ltd., London (GB)

(72) Inventors: David Julian Mann, London (GB); Gregory Benedict Craven, London (GB); Stefan Matthies, London (GB); Alan Armstrong, London (GB)

(73) Assignee: Imperial College Innovations Ltd., London (GB)

( * ) Notice: Subject to any disclaimer, the term of this patent is extended or adjusted under 35 U.S.C. 154(b) by 230 days.

(21) Appl. No.: 16/326,298

(22) PCT Filed: Aug. 18, 2017

(86) PCT No.: PCT/GB2017/052456
§ 371 (c)(1),
(2) Date: Feb. 18, 2019

(87) PCT Pub. No.: WO2018/033753
PCT Pub. Date: Feb. 22, 2018

(65) Prior Publication Data
US 2019/0293641 A1 Sep. 26, 2019

(30) Foreign Application Priority Data

Aug. 18, 2016 (GB) ...................... 1614152

(51) Int. Cl.
*G01N 33/557* (2006.01)

(52) U.S. Cl.
CPC ....... *G01N 33/557* (2013.01); *G01N 2500/04* (2013.01)

(58) Field of Classification Search
CPC .................. G01N 33/557; G01N 2500/04
See application file for complete search history.

(56) References Cited

U.S. PATENT DOCUMENTS

2002/0022233 A1   2/2002   Wells et al.

FOREIGN PATENT DOCUMENTS

JP    2004514891 A   5/2004
WO   2005/034840 A2  4/2005

OTHER PUBLICATIONS

Hallenbeck et al. Targeting non-catalytic cysteine residues through structure-guided drug discovery. Curr. Top Med Chem. 2017, vol. 17, pp. 4-15 (Year: 2017).*
Lodge et al. FP tethering: a screening technique to rapidly identify compounds that disrupt protein-protein interactions. Medchemcomm. 2014, vol. 5, pp. 370-375. (Year: 2014).*

(Continued)

*Primary Examiner* — Shafiqul Haq
(74) *Attorney, Agent, or Firm* — Elmore Patent Law Group, P.C.; Carolyn S. Elmore; Mahreen Chaudhry Hoda

(57) ABSTRACT

The present invention relates to a method of measuring the rate of reaction between a target molecule and a ligand candidate, ligands of interest identified according to this method and drugs developed from such ligands. The present invention also relates to a method of measuring the rate of reaction between a thiol and a molecule capable of reacting with said thiol.

22 Claims, 12 Drawing Sheets
Specification includes a Sequence Listing.

(56) References Cited

OTHER PUBLICATIONS

Kathman et al. A fragment-based method to discover irreversible covalent inhibitors of cysteine protease. J. Med. Chem. 2014, vol. 57, pp. 4969-4975. (Year: 2014).*
Winther et al. Quantification of thiols and disulfides. Biochim Biophys Acta. Authur manuscript; availble Feb. 1, 2015, pp. 1-26 (Year: 2015).*
Erlanson et al. Discovery of a potent and highly selective PDK1 inhibitor via fragment-based drug discovery. Bioorganic and Medicinal Chemistry Letters 2011, vol. 21, pp. 3078-3083. (Year: 2011).*
Nonoo et al. Kinetic templete-guided tethering of fragments. ChemMedChem 2012, vol. 7, pp. 2082-2086. (Year: 2012).*
Erlanson, D.A, Wells, J.A. and Braisted, A.C. 2004. Tethering: Fragment-Based Drug Discovery. Annu. Rev. Biophys. Biomol. Struct., 33, 199-223.
Kathman, S.G., Xu, Z. and Statsyuk, A.V. 2014. A Fragment-Based Method to Discover Irreversible Covalent Inhibitors of Cysteine Proteases. J. Med. Chem., 57, 4969-4974.
Nonoo, R.H, Armstrong, A. and Mann, D.J. 2012. Kinetic Template-Guided Tethering of Fragments. Chem.Med. Chem., 7, 2082-2086.
Allen, C. E.; Curran, P. R.; Brearley, A. S.; Boissel, V.; Sviridenko, L.; Press, N. J.; Stonehouse, J. P.; Armstrong, A. 2015. Efficient and Facile Synthesis of Acrylamide Libraries for Protein-Guided Tethering. Org. Lett., 17, 458-460.

Hong, V.; Kislukhin, A. A.; Finn, M. G. 2009. Thiol-Selective Fluorogenic Probes for Labeling and Release J. Am. Chem. Soc., 2009, 131 (29), 9986-9994.
Yl, L, Li H, Sun L, Liu L, Zhang C, Xi Z 2009. A highly sensitive fluorescence probe for fast thiol-quantification assay of glutathione reductase Angew Chem Int Ed Engl. 48(22):4034-7.
Chen, X.; Zhou, Y.; Peng, X. and Juyoung, Y., 2010. Fluorescent and colorimetric probes for detection of thiols. Chem. Soc. Rev., 39, 2120-2135.
Alzahrani, E.; Welham, K. 2014. Fabrication of a TCEP-immobilised monolithic silica microchip for reduction of disulphide bonds in proteins Anal. Methods, 6, 558-568.
Page, J.D., et al., "Inhibition of Inosine Monophosphate Dehydrogenase by Sesquiterpene Lactones," Biochimica et Biophysica Acta vol. 926, pp. 186-194, 1987.
Kathman, S. et al., "Covalent Tethering of Fragments for Covalent Probe Discovery", Med. Chem. Comm., vol. 17, No. 4, Jan. 28, 2016, 576-585.
Riener, C. et al., "Quick Measurement of Protein Sulfhydryls with Ellman's Reagent and with 4,4'-dithiodipyridine", Anal. Bioanal. Chem., 373, Jun. 6, 2002, 266-276.
Reddick, J., et al., "Relative Rates of Michael Reactions of 2'(Phenethyl)thiol with Vinyl Sulfones, Vinyl Sulfonate Esters, and Vinyl Sulfonamides Relevant to Vinyl Sulfonyl Cysteine Protease Inhibitors," Organic Letters vol. 5, No. 11, 1967-1970 (2003).

* cited by examiner $k_{Cdk2}/k_{GSH}$ (EL-1071) = 8.5

$K_d$ = 1.2 mM
$k_2$ = 0.009427 min$^{-1}$

SEQUENCE LISTING

<160> NUMBER OF SEQ ID NOS: 1

<210> SEQ ID NO 1
<211> LENGTH: 13
<212> TYPE: PRT
<213> ORGANISM: Homo sapiens

<400> SEQUENCE: 1

Leu Tyr Leu Val Cys Glu Phe Leu His Gln Asp Leu Lys
1               5                   10

ASSAY FOR MEASURING A RATE OF REACTION BETWEEN A TARGET AND A LIGAND CANDIDATE

The present invention relates to a method of measuring the rate of reaction between a target molecule and a ligand candidate, ligands of interest identified according to this method and drugs developed from such ligands. The present invention also relates to a method of measuring the rate of reaction between a thiol and a molecule capable of reacting with said thiol.

BACKGROUND

New drugs are the product of a long development process, the first step of which is often the screening of libraries of ligands candidates which bind, reversibly or irreversibly, to a target molecule. In the past, huge libraries of compounds were screened against a target molecule using high-throughput screening (HTS) methods in the hope that one or more successful leads would emerge.

In recent years, a fragment-based approach to drug discovery (FBDD) has emerged as an alternative approach to traditional lead identification via HTS. Unlike HTS, FBDD identifies smaller compounds, "fragments", which bind to different parts of a biological target.

Due to the small number of interactions made with the target molecule, many fragments have weak intrinsic affinities for their targets. The weak interactions between a fragment and its target molecule can be difficult to detect. Furthermore, screens can be complicated by the necessity of applying fragments in high concentrations, which leads to issues with solubility, compound aggregation, protein denaturation and ligand binding at multiple sites.

These issues have been overcome using tethering techniques, whereby fragments modified to comprise electrophilic functional groups form covalent bonds with nucleophilic groups on the surface of the target molecule. Because the covalent bond is formed at a pre-determined site on the target molecule, for example a native or non-native cysteine, the stoichiometry and binding location are known for ligands that are identified by this method. The formation of the covalent bond between the target molecule and the ligand candidate amplifies the affinity of the fragment for the target molecule, enabling detection at lower concentrations.

Initially, tethering techniques focused on the formation of reversible covalent bonds[1,2,3]. A distribution of target molecule-ligand conjugates is produced where the most thermodynamically stable conjugate dominates the mixture. Tethering techniques involving the formation of irreversible covalent bonds have been developed in more recent years[4,5], making use of functional groups such as vinyl sulphonamides, acrylamides and aminomethyl methyl acrylates. With irreversible tethering, the resulting target molecule-ligand conjugate mixture is dominated by the ligand candidate which reacts most quickly with the target molecule.

For both reversible and irreversible tethering techniques, mixtures of fragments, typically between 5 and 10, were incubated with the target molecule, with the conjugate dominating the mixture representing the most promising lead. Typically, the conjugates were identified using intact protein mass spectrometry (MS) where, due to the heterogeneity of the reaction mixture, quantification can be difficult. Importantly for irreversible tethering, intrinsic fragment reactivity can influence the rate of conjugate formation, such that the dominating conjugate is not necessarily the most promising lead. Therefore, ligand candidates in a particular screening pool must exhibit very similar intrinsic reactivities as well as sufficiently differential molecular weights to facilitate unambiguous hit identification. Predetermination of intrinsic fragment reactivity with a model thiol, such as glutathione, typically relies on either mass spectrometry or nuclear magnetic resonance (NMR) performed on individual candidates, resulting in low throughput. In order to by-pass this reactivity determination, candidates would have to be selected from within a similar region of chemical space, such that their intrinsic reactivity is similar. This reduces the diversity of the types of ligand candidates that can be screened. Furthermore, analysis of tethering by MS requires sequential measurements of fragment pools, significantly reducing throughput.

There is therefore a need in the art to provide a high-throughput method for screening ligand candidates individually against a target molecule which provides quantitative data allowing a direct comparison between different ligand candidates, upon normalisation of intrinsic reactivity against a model.

SUMMARY OF THE INVENTION

The present invention solves the problems described above by providing a method of measuring the rate of reaction between a target molecule and a ligand candidate using a kinetic thiol consumption assay, wherein the target molecule comprises a thiol group within or near a binding site of interest and the ligand candidate comprises a functional group capable of forming an irreversible covalent bond with the thiol group. This method provides quantitative information which allows direct comparison between ligand candidates. This method can be used to identify ligands of interest, which can then be developed, for example, into drugs. The kinetic thiol consumption assay also has potential uses beyond the identification of ligands of interest.

FIGURES

The present invention will be described further with reference to the accompanying, non-limiting drawings, in which:

FIG. 1 is a pictographic representation of the formation of a target molecule-ligand conjugate. In templated capture, the ligand candidate bonds non-covalently to the binding site of interest on the target molecule, and an irreversible covalent bond is then formed between the thiol group (SH) of the target molecule and the functional group (or "capture group") of the ligand candidate. In non-templated capture, an irreversible covalent bond is formed between the thiol group of the target molecule and the functional group of the ligand candidate without any preceding non-covalent binding of the ligand candidate to the binding site of interest.

FIG. 2(a) is an illustration of the formation of a model thiol-ligand conjugate, in particular a glutathione-ligand conjugate (top) and the formation of a target molecule-ligand conjugate, in particular a protein-ligand conjugate (bottom), wherein the ligand candidates comprise an acrylamide functional group.

FIG. 2(b) is an exemplary plot of fragment frequency over rate enhancement ($k_{target}/k_{model}$). The vertical dotted line represents the chosen threshold level for rate enhancement. In most cases, fragments falling to the left of the line (below the chosen threshold level) represent fragments with non-templated reactivity. Similarly, in most cases, fragments falling to the right of the line (above the chosen threshold level) represent fragments with templated reactivity which have a significantly enhanced rate constant with the target molecule relative to the model thiol and are classified as "hits".

Figure 5:
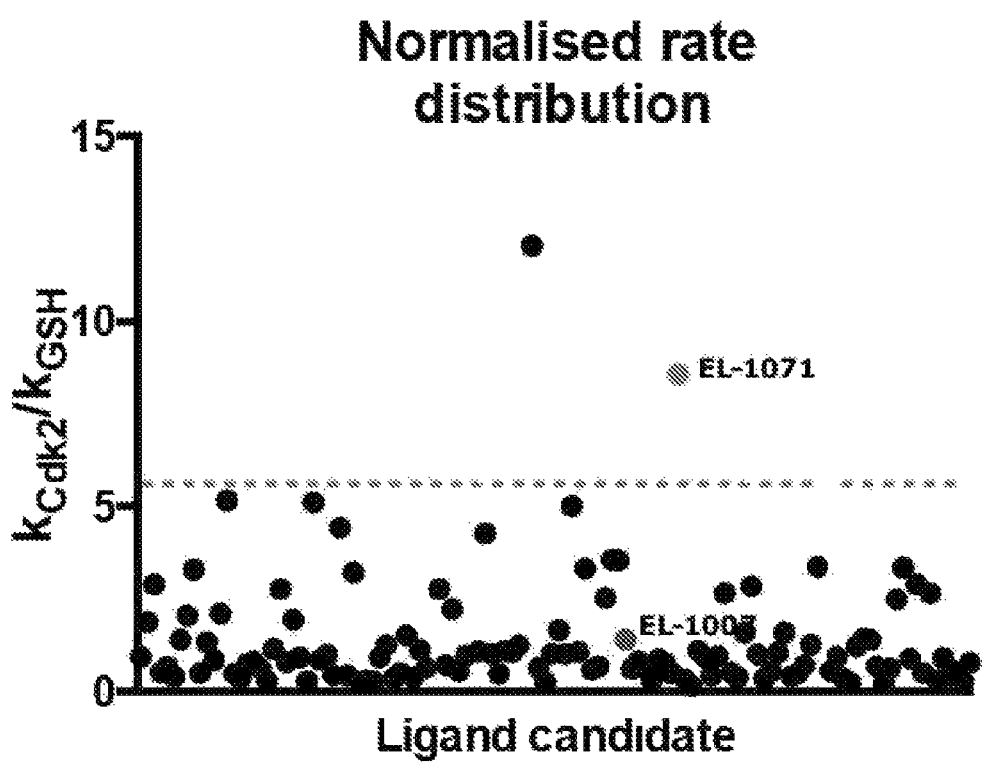

FIG. 5 shows a normalised rate distribution created in Example 1, showing the rate enhancement ($k_{Cdk2}/k_{GSH}$) for each of the 120 ligand candidates tested. The horizontal dotted line represents the chosen threshold level for rate enhancement, above which ligand candidates are classified as "hits". Two exemplary ligand candidates are labelled: a negative compound (EL-1007) and a hit fragment (EL-1071).

Figure 6:
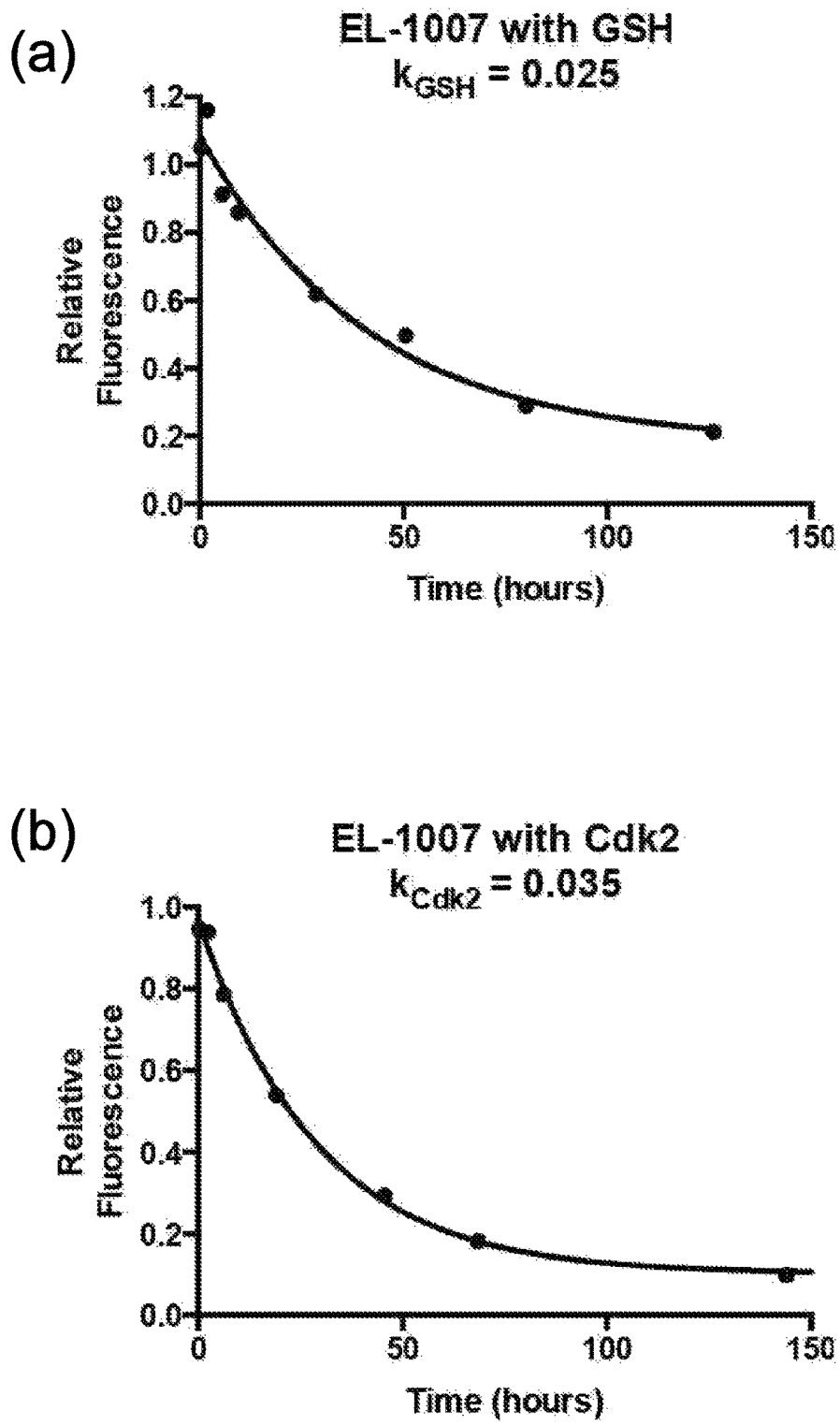

FIG. 6(a) is a plot of relative fluorescence over time for ligand candidate EL-1007 with the model thiol glutathione (GSH). This data was used to calculate a rate constant ($k_{GSH}$) of 0.025.

FIG. 6(b) is a plot of relative fluorescence over time for ligand candidate EL-1007 with the target molecule, cyclin-dependent kinase 2 (Cdk2). This data was used to calculate a rate constant ($k_{Cdk2}$) of 0.035. Dividing $k_{Cdk2}$ by $k_{GSH}$ produces a rate enhancement of 1.4.

Figure 7:
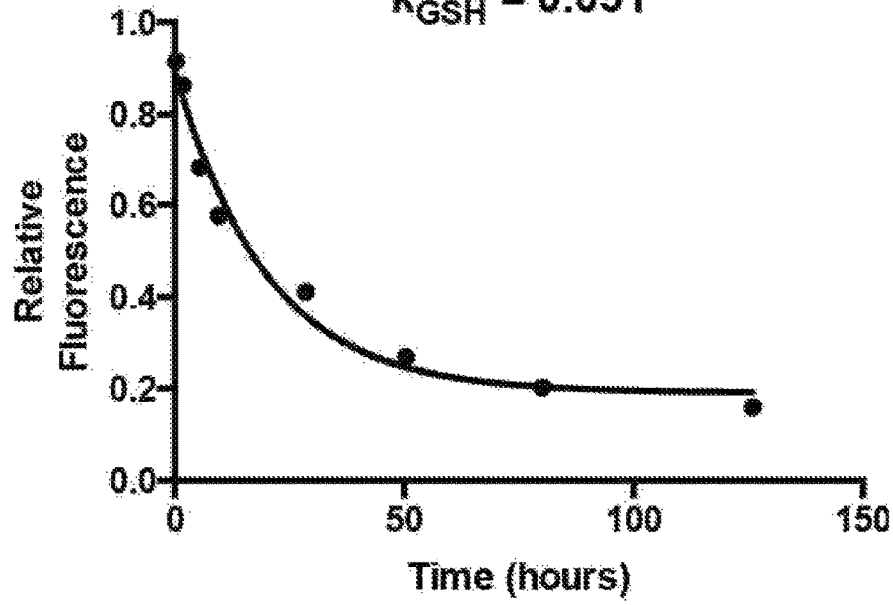
Figure 7:
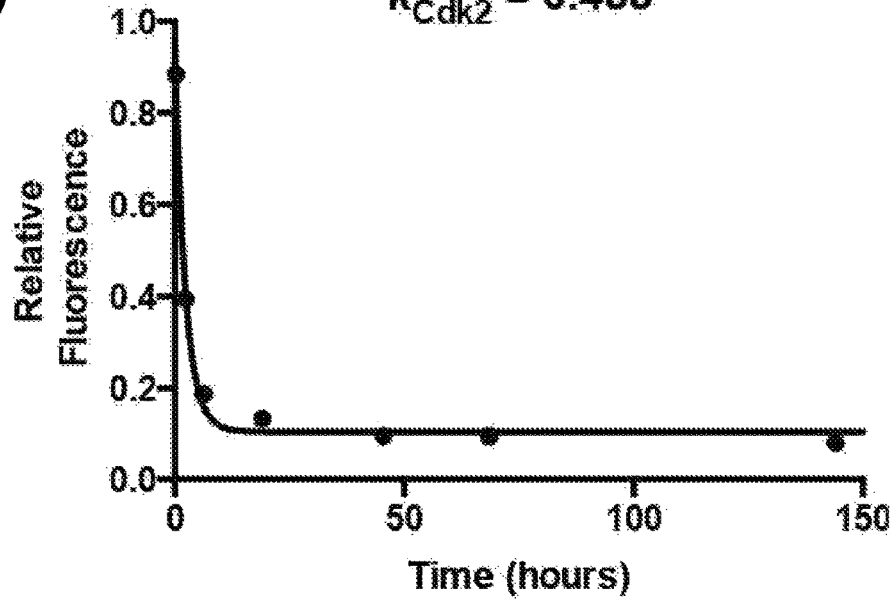

FIG. 7(a) is a plot of relative fluorescence over time for ligand candidate EL-1071 with the model thiol glutathione (GSH). This data was used to calculate a rate constant ($k_{GSH}$) of 0.051.

FIG. 7(b) is a plot of relative fluorescence over time for ligand candidate EL-1071 with the target molecule, cyclin-dependent kinase 2 (Cdk2). This data was used to calculate a rate constant ($k_{Cdk2}$) of 0.433. Dividing $k_{Cdk2}$ by $k_{GSH}$ produces a rate enhancement of 8.5.

Figure 8:
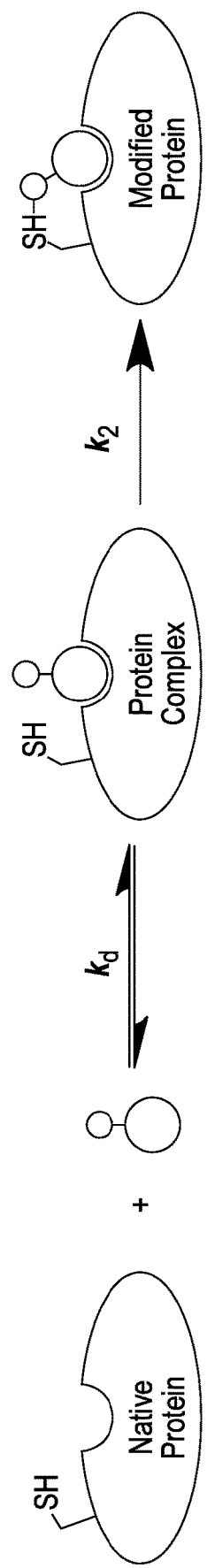

FIG. 8 is an illustration of the two-step mechanism for the formation of a target molecule-ligand conjugate.

Figure 9:
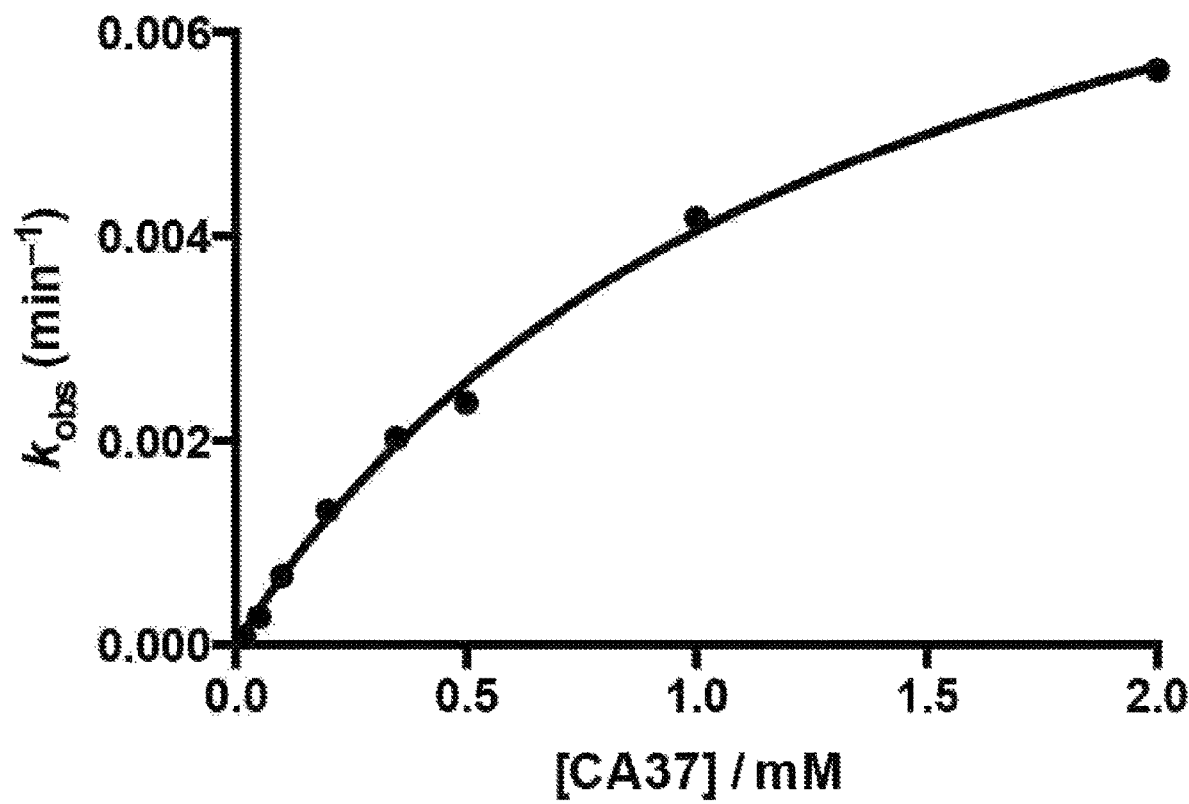

FIG. 9 is a plot of observed rate constant versus hit ligand candidate (CA37) concentration identified against Cdk2 (C177A, F80C).

Figure 10:
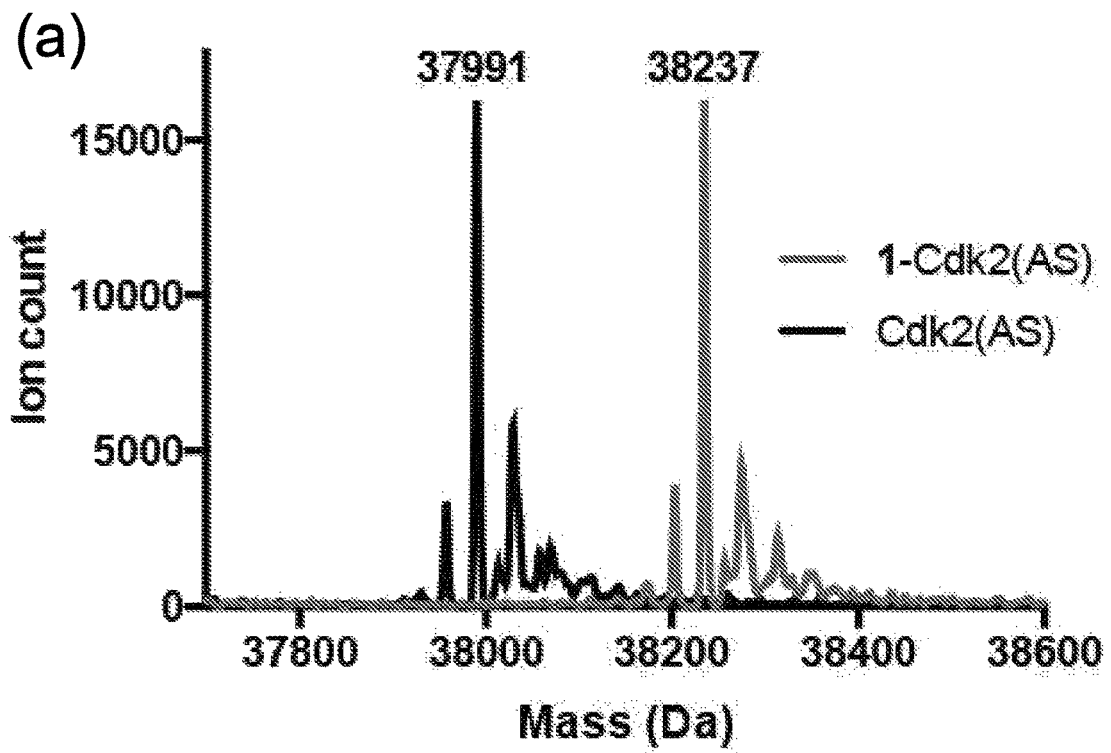
Figure 10:
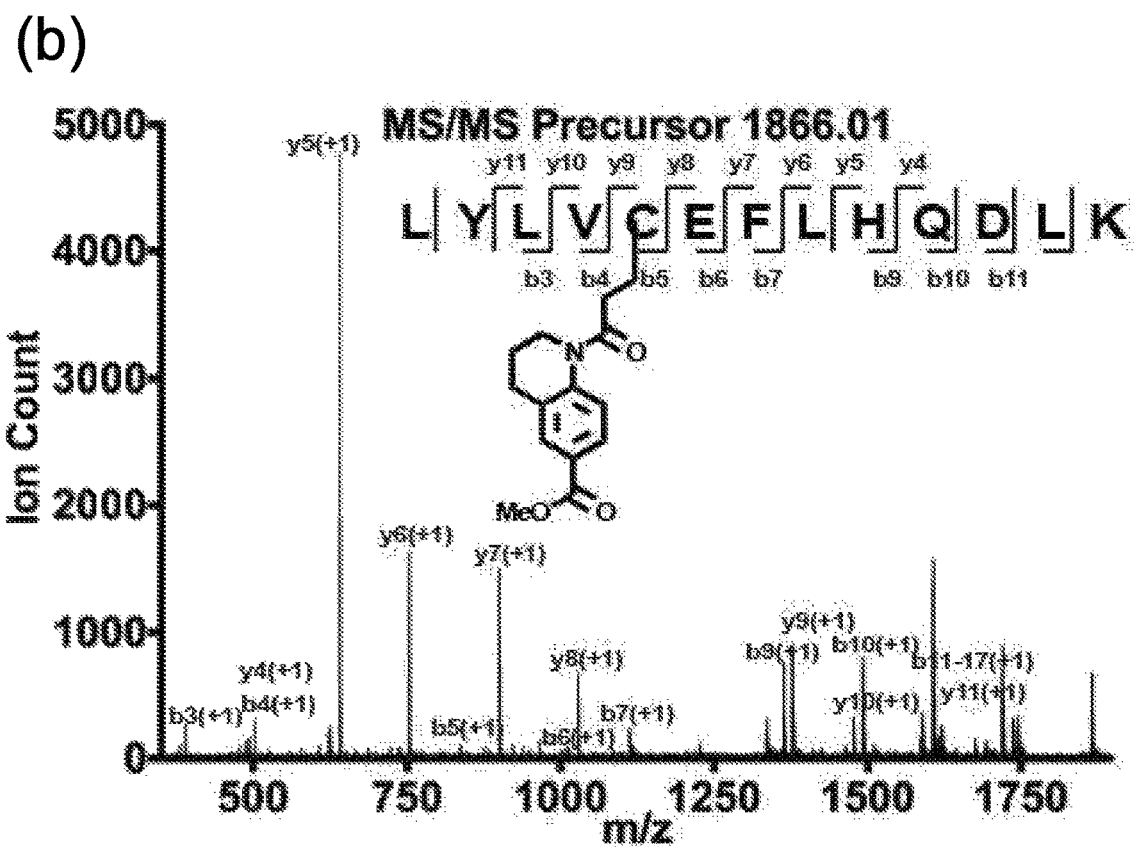
Figure 10:
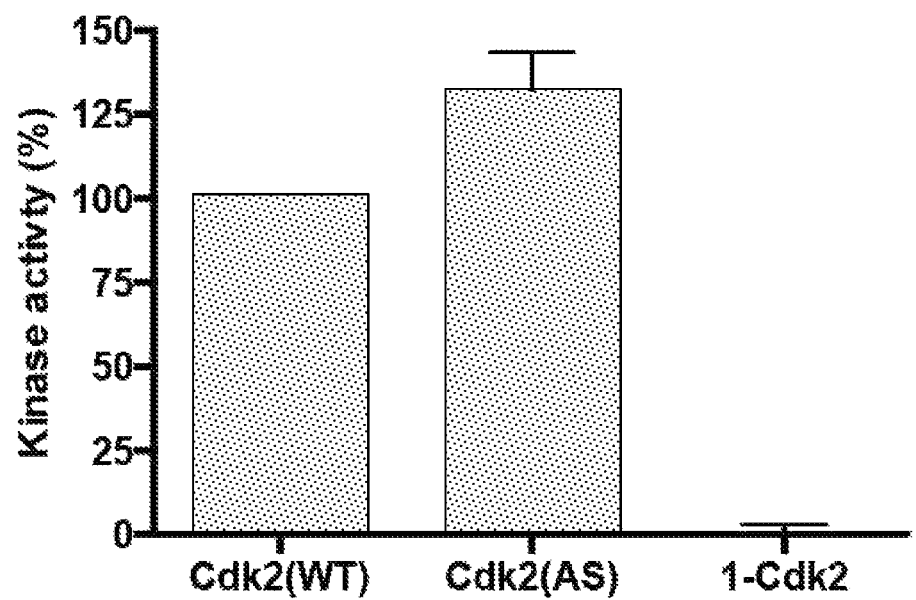

FIG. 10(a) is an intact protein mass spectrometry mass spectrum cross-validating the complete monomodification of Cdk2(F80C, C177A) by EL1071. (In this figure Cdk2 (AS)=Cdk2(F80C, C177A), 1=EL1071.)

FIG. 10(b) is a tandem mass spectrometry mass spectrum confirming the site of modification as F80C, obtained by digesting the 1-Cdk2(AS) complex with trypsin and sequencing the resulting peptides.

FIG. 10(c) is a plot comparing the kinase activity of Cdk2(WT), Cdk2(AS) and 1-Cdk-2(AS).

Figure 11:
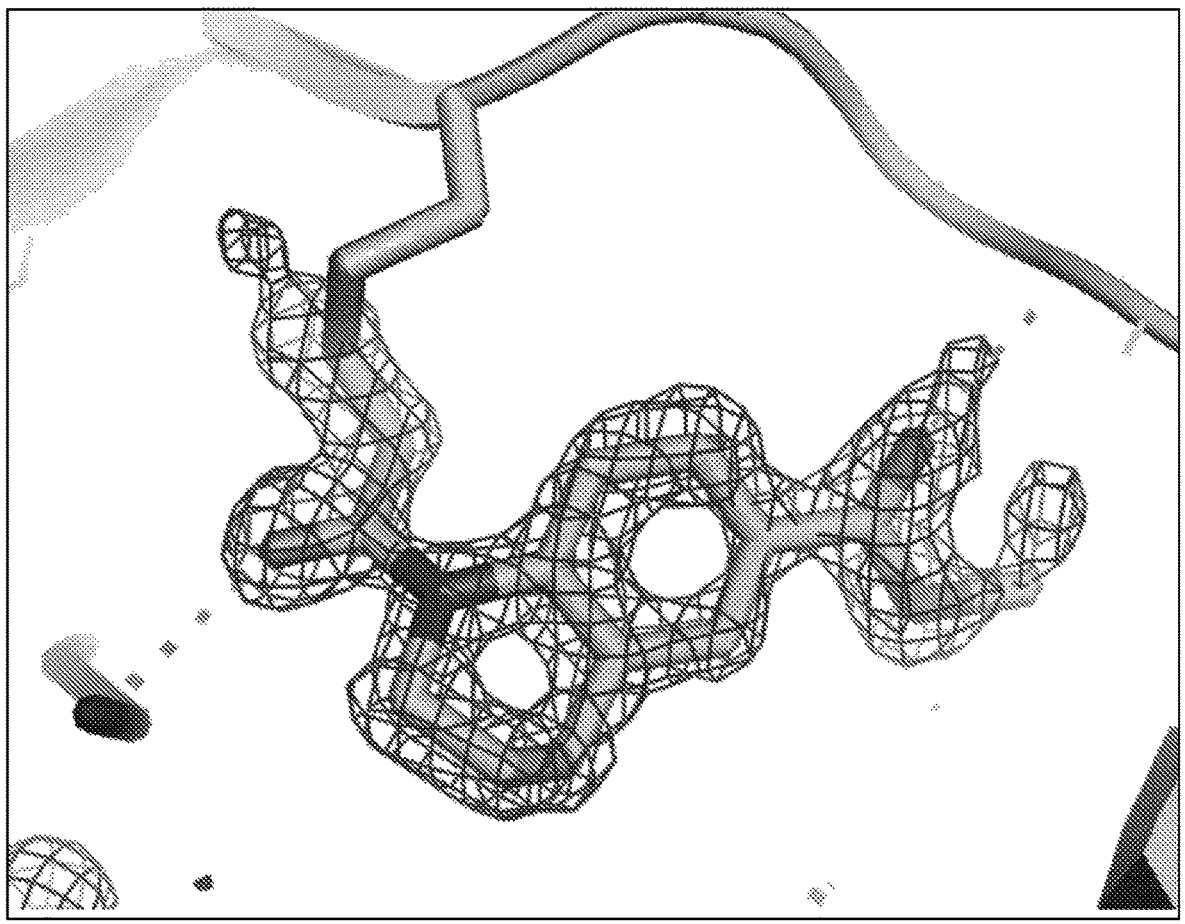

FIG. 11 is an illustration of the structure of crystallised 1-Cdk2(AS) complex determined by X-ray crystallography, confirming that the ligand binds to the cysteine residue at F80C

DETAILED DESCRIPTION

A first aspect of the present invention provides a method of measuring the rate of reaction between a target molecule and a ligand candidate comprising the steps of:
a) providing a target molecule comprising a binding site of interest and a thiol group within or near the binding site of interest;
b) contacting the target molecule with a ligand candidate in a reaction mixture, wherein the ligand candidate comprises a functional group which is capable of forming an irreversible covalent bond with said thiol group;
c) forming an irreversible covalent bond between the thiol group of the target molecule and the functional group of the ligand candidate, thereby forming a target molecule-ligand conjugate;
d) contacting the reaction mixture or an aliquot thereof with a thiol quantification reagent at a defined time point during the reaction, wherein the thiol quantification reagent is capable of bonding to free thiol groups to form a quantification conjugate which provides the reaction mixture or aliquot thereof with a biophysical property assessable by a biophysical method;
e) measuring the biophysical property of the reaction mixture or aliquot thereof; and
f) calculating the rate of reaction between the target molecule and the ligand candidate.

This method allows the calculation of the rate of reaction between a target molecule and a ligand candidate for each individual ligand candidate screened, providing quantitative information that allows a direct comparison between different ligand candidates.

The rate of reaction calculated can be used to obtain or approximate a rate constant for the formation of the target molecule-ligand conjugate.

The target molecule comprises a binding site of interest, namely a site to which a specific ligand binds. Typically, the molecular interactions between the ligand and the binding site of interest on the target molecule are non-covalent and include hydrogen bonds, van der Waals interactions and electrostatic interactions.

The target molecule also comprises a thiol group within or near the binding site of interest.

A thiol is an organosulfur compound that contains a carbon-bonded sulfhydryl (—C—SH or R—SH) group (where R may represents an organic moiety or biomolecule) which exists predominantly as the thiolate anion at physiological pH and under most screening conditions.

In accordance with the present invention, the thiol group is considered to be near the binding site of interest if it is close enough to the binding site of interest to allow the formation of a covalent bond between the thiol group and a functional group on the ligand candidate, when the ligand candidate bonds to the binding site of interest. Preferably, if ligand candidate binds to the binding site of interest, it concomitantly brings the functional group on the ligand candidate into sufficiently close proximity with the thiol group to result in covalent capture of the ligand candidate.

The formation of this covalent bond following the binding of the ligand candidate with the binding site of interest on the target molecule is termed "templated capture". The formation of this covalent bond in the absence of the binding of the ligand candidate with the binding site of interest on the target molecule is termed "non-templated capture". Non-templated capture usually occurs when the ligand candidate has no, or negligible, binding affinity for the binding site of interest. Templated capture occurs when the ligand candidate has affinity for the target molecule, and results in an enhancement in the rate of reaction between the ligand candidate and the target molecule.

The thiol group may be 10 Å or less, for example between 5 and 10 Å, from the binding site of interest. The thiol group may be further from the binding site of interest, for example where a linker is included between the ligand candidate and the functional group.

The thiol group in question must be accessible for covalent bond formation with the functional group once the ligand candidate has bound to the target molecule. Preferably, the thiol group is relatively surface-exposed.

The thiol group may be endogenous to the target molecule. Alternatively, the target molecule may have been modified to include the thiol group. Those of skill in the art will be familiar with various recombinant, chemical, synthetic or other techniques that can routinely be employed to modify a target molecule such that it possesses a thiol group at or near a binding site of interest. Such techniques include site-directed mutagenesis, cassette mutagenesis and or the incorporation of non-natural amino acids into proteins using an expanded genetic code.

The thiol group is preferably provided by a thiol-containing amino acid residue, preferably a cysteine residue. Preferably, the thiol group is provided by a surface-exposed cysteine residue. As discussed in respect of the thiol group, above, a cysteine residue providing a thiol group may be endogenous to the target molecule or the target molecule may have been modified to include the cysteine residue. Where the cysteine residue is endogenous, it may be catalytic or non-catalytic.

The target molecule, when initially obtained or after modification, may comprise more than one free thiol group accessible for covalent bond formation with the functional group on the ligand candidate. For example, the target molecule may comprise more than one surface-exposed cysteine residue. Preferably, the target molecule comprises only a limited number of free thiol groups which may potentially serve as covalent binding sites for a ligand candidate. The target molecule may comprise no more than 5 free thiol groups, no more than 4 free thiol groups, no more than 3 free thiol groups, no more than 2 free thiol groups, or only 1 free thiol group. The target molecule may be initially obtained or selected such that it already possesses the desired number of free thiol groups or may be modified to possess the desired number of free thiol groups. The target molecule may, of course, include any number of internal thiol groups which are not accessible for covalent bond formation with the functional group on the target molecule.

The target molecule typically comprises a molecule of interest, for example a potential target effected by a reversible or irreversible inhibitor. The target molecule may be a biological target in the context of drug discovery or biochemical investigation.

Preferably, the target molecule is selected from the group consisting of a protein or a derivative thereof, for example a polypeptide, a nucleoprotein, a glycopeptide or a phosphoprotein.

The target molecule may be selected from the group consisting of an enzyme, a hormone, a transcription factor, a receptor, a ligand for a receptor, a growth factor, an immunoglobulin, a steroid receptor, a nuclear protein, a signal transduction component, an allosteric enzyme regulator or the like.

Examples of enzymes include kinase, phosphatase, GTPase, protease, ligase, caspase, glycosyltransferase, glycoside hydrolase, lipid transferase and reductase enzymes.

Exemplary target molecules include various cyclin-dependent kinase 2 (Cdk2) mutants, each possessing a single surface-exposed cysteine residue.

In the context of the present invention, a "ligand candidate" is a compound that comprises a functional group which is capable of forming an irreversible covalent bond with the thiol group on the target molecule. A ligand candidate may or may not have intrinsic binding affinity for the target molecule. Once it is determined that a ligand candidate also has intrinsic binding affinity for the target molecule i.e. that it can bind to the binding site of interest on the target molecule, the ligand candidate may be termed a "ligand".

The ligand candidate may comprise a small molecule, which is classified as a molecule with a molecular weight of 900 Da or less. Preferred small molecules have a weight of less than 500 Da. The ligand candidate may alternatively comprise a biopolymer-based ligand or any combination of synthetic or endogenous molecules.

The ligand candidate may also comprise a fragment of a molecule. Fragments have a much better chance of exhibiting "high-quality" interactions with a defined binding site. Fragments which are found to have an affinity with the target molecule, even if only a weak affinity, can then be grown or combined to produce a lead with a higher affinity.

Preferably, the fragment has a relatively low molecular weight, preferably a molecular weight of 300 Da or less, 250 Da or less, 200 Da or less, 150 Da or less or 100 Da or less.

Preferably, the fragment follows the "rule of three" (the molecular weight of a fragment is <300 Da, the c Log P is ≤3, the number of hydrogen bond donors is ≤3 and the number of hydrogen bond acceptors is ≤3).

Preferably, the fragment comprises at least one functionality selected from the group consisting of aliphatic, heteroatom containing, cyclic, aromatic and heteroaromatic moieties.

The use of a target molecule comprising a binding site of interest and a thiol group within or near the binding site of interest allows the site-directed discovery of low molecular weight fragments that bind weakly to defined protein surfaces.

The ligand candidates of the present invention may comprise drug-like molecules or drug-like fragments. Such molecules and fragments are well known in the art and have drug-like properties such as low molecular weight and desirable physiochemical and pharmacological properties, as well as substructures with known chemical or pharmacological properties.

Preferably, the ligand candidate is selected from the group comprising organic molecules or other sequence-specific binding molecules such as peptides, peptidomimetics, complex carbohydrates or other oligomers of individual units or monomers.

As mentioned above, the ligand candidate comprises a functional group which is capable of forming an irreversible covalent bond with the thiol group on the target molecule. Such a functional group may also be termed a "capture group" or "warhead".

Preferably, the functional group is an electrophile.

Suitable electrophiles include acrylamide, acrylate, α,β-unsaturated ketone, vinyl sulfonamides, vinylsulfone, vinylsulfonate, α-halogenated carbonyl derivatives such as α-chloroketones and α-chloroacetamides, epoxides, nitrile derivatives (for example A-aminonitriles), $S_NAr$ substrates (for example aromatic rings bearing electron withdrawing groups) and substituted derivatives thereof.

Preferred electrophiles include Michael acceptors, namely a, n-unsaturated carbonyl or nitrile compounds which undergo a 1,4-addition reaction with resonance-stabilized carbon nucleophiles. Particularly preferred Michael acceptors include acrylamides, methyl acrylates and vinyl sulphonamides.

Those of skill in the art will be familiar with various techniques that can routinely be employed to attach or tether a functional group such as acrylamide to a molecule or fragment thereof. For example, a suitable technique for attaching a functional group to a target molecule of the present invention can be found in Allen, C. E. et al.[6], which is incorporated herein by reference.

The method of the first aspect of the present invention includes a step of contacting the target molecule with a ligand candidate in a reaction mixture, resulting in the formation of an irreversible covalent bond between the thiol group of the target molecule and the functional group of the ligand candidate, thereby forming a target molecule-ligand conjugate. This target molecule-ligand conjugate may have been formed as a result of templated or non-templated capture (i.e. with or without the binding of the ligand candidate to the binding site of interest on the target molecule). The term "ligand" is used in this context merely for the purposes of brevity. The term "target molecule-ligand candidate conjugate" could equally be used.

The target molecule may be contacted with a ligand candidate under any suitable reactions conditions, which will be known to one of skill in the art.

The reaction may take place within any suitable container, for example a well of a reaction plate.

The target molecule may be added to the container prior to the addition of the ligand candidate. Alternatively, the ligand candidate may be added to the container prior to the addition of the target molecule. In either case, the ligand candidate and the target molecule are combined to create the reaction mixture.

Any suitable quantity of target molecule may be used. The quantity of target molecule added may correspond to 1 to 10 µM of the target molecule, for example approximately 5 µM of the target molecule.

The target molecule may be in a suitable buffer, for example a degassed phosphate buffer (pH 8). Where a buffer is used, the combined quantity of buffer and target molecule used may be in the range pL to µL, for example 10 pL to 300 µL, 10 pL to 100 nL, 10 pL to 100 pL, 100 pL to 100 nL, 10 µL to 300 µL, 100 µL to 250 µL, 150 µL to 200 µL, or approximately 150 µL.

Preferably, the target molecule and the ligand candidate are contacted in the presence of a reducing agent. Any suitable reducing agent may be used, for example tris-(2-carboxyethyl)phosphine (TCEP) or dithiothreitol (DDT).

The reducing agent may be solubilised or immobilised depending upon the biophysical property being assessed. Preferably, where the biophysical property being assessed is fluorescence, the reducing agent is immobilised. The use of an immobilised reducing agent allows miniaturisation of the assay such that thiol oxidation does not obscure the true signal. The reducing agent may be agarose-bound.

Any suitable quantity of reducing agent may be used. For example, 2% v/v of immobilised agent may be used, as in the examples below.

Where a reducing agent is used, the target molecule may be incubated with the reducing agent prior to the addition of the ligand candidate, in order to ensure that the thiol of the target molecule is fully reduced. As such, any reduction in thiol signal during the thiol quantification reaction can be attributed to the reaction with the ligand candidate. For example, the target molecule may be incubated with the reducing agent at 4° C. for 1 hour, as in the examples below.

The ligand candidate may be added in a suitable solvent, such as dimethyl sulfoxide (DMSO). The ligand candidate may be added in any suitable amount. The ligand candidate may be provided in a sufficient amount to yield a final concentration of 100 to 1000 µM of the ligand candidate, for example approximately 500 µM of the ligand candidate.

Preferably, the ligand candidate is added in a much higher concentration than the target molecule. Preferably, the ligand candidate is provided in excess, most preferably in more than 10-fold excess.

The method according to the first aspect of the present invention involves measuring the rate of reaction between the target molecule and the ligand, in other words the rate of formation of the target molecule-ligand conjugate, using a novel assay. This assay might be termed a "kinetic thiol consumption assay" as it relies upon the measurement of the rate of consumption of the thiol group in the target molecule to indicate the rate of formation of the target molecule-ligand conjugate. As used herein, the consumption of the thiol group refers to the chemical modification of the thiol group upon formation of the irreversible covalent bond with the functional group on the ligand candidate.

The rate of consumption of the thiol group in the target molecule is inferred by measuring the relative amount of "free" (i.e. unreacted) thiol groups in the reaction mixture or an aliquot thereof at a single or a plurality of time points during the reaction, using a quench assay compared to a control. Any decrease in the relative amount of free thiol groups over time is taken to be a result of the consumption of the free thiol groups in the formation of the irreversible covalent bond between the target molecule and the ligand candidate.

The relative amount of free thiol groups in the reaction mixture or aliquot thereof at a particular point in time is measured using a thiol quantification reagent which is capable of bonding to free thiol groups to form a quantification conjugate which provides the reaction mixture or an aliquot thereof with a biophysical property assessable by a biophysical method. The biophysical property provides an indication of the relative amount of quantification conjugate in the reaction mixture or an aliquot thereof.

If desired, the concentration of quantification conjugate in the reaction mixture or aliquot thereof can be determined from the measurement of the biophysical property, using methods that are well known to the skilled person using an appropriate calibration method and which depend upon the thiol quantification reagent used.

The biophysical property may be, for example, fluorescence, fluorescence polarisation, fluorescence anisotropy or the absorbance of visible light at a particular wavelength.

The quantification conjugate itself may have the assessable biophysical property. Alternatively, a derivative of the quantification conjugate may have the assessable biophysical property, or the production of the quantification conjugate may result in the production of a compound with the assessable biophysical property.

Preferably, the thiol quantification reagent is a thiol-reactive dye.

Many reagents and methods have been developed for the quantitative assay of thiols. Thiol-reactive reagents include iodoacetamides, maleimides, benzylic halides and bromomethylketones, which react by S-alkylation of thiols to generate stable thioether products. Arylating reagents such as NBD halides react with thiols by a similar substitution of the aromatic halide by the nucleophile. Disulfide and thiosulphate based dyes allow reversible thiol modification for thiol quantification.

Maleimides or maleimide derivatives are preferred, for example N-(7-dimethylamino-4-methylcoumarin-3-yl)maleimide (DACM), fluorescein-5-maleimide and particularly 7-diethylamino-3-(4'-maleimidylphenyl)-4-methylcoumarin (CPM). These thiol quantification reagents are not appreciably fluorescent until after conjugation with thiols. The thiol is added across the double bond of the maleimide to yield a highly fluorescent thioether.

Ellman's reagent (5,5'-dithiobis-(2-nitrobenzoic acid) or DTNB) might also be used. Thiols react with this compound, cleaving the disulfide bond to give 2-nitro-5-thiobenzoate (TNB$^-$), which ionizes to the TNB$^{2-}$ dianion in water at neutral and alkaline pH. This TNB$^{2-}$ ion has a yellow color which absorbs visible light at 412 nm.

The entire reaction mixture, a substantial proportion thereof, or just an aliquot thereof may be contacted with a thiol quantification reagent in step d) of the method according to the first aspect.

If aliquots are used they may comprise any suitable volume. Aliquot volumes may be in the range of pL to µL, for example 1 to 10 µL, 1 to 8 µL, 1 to 5 µL or approximately 3 µL. Typically, each aliquot comprises 1 to 5% of the total reaction volume.

Preferably, the reaction mixture or a substantial proportion thereof is removed from the container in which target molecule is contacted with the ligand candidate, or aliquots are removed from the reaction mixture, in such a manner as to avoid or minimise the risk of transferring any immobilized reducing agent to the quench plate.

Preferably, each aliquot is transferred into a separate well of a quench plate.

Preferably, each quench plate contains an excess of the thiol quantification reagent. The thiol quantification reagent may be in a buffer solution, for example a degassed phosphate buffer solution (pH 7.5).

Preferably, the reaction mixture or aliquot thereof is incubated in the quench plate for a suitable time period before the biophysical property is measured. The reaction mixture or aliquot thereof may be incubated for 0.1 to 2 hours, for example approximately 1 hour. Incubation may be conducted at any suitable temperature, for example at room temperature.

The biophysical property of the reaction mixture or aliquot thereof may be measured using any suitable biophysical method. For example, fluorescence or fluorescence polarisation may be measured using a fluorometer such as an EnVision plate reader. Absorbance of light at a particular wavelength may be measured using a spectrophotometer.

The concentration of quantification conjugate in the reaction mixture or aliquot thereof reflects the concentration of "free" thiol groups in the reaction mixture or aliquot thereof at a particular time point, which in turn reflects the concentration of unreacted target molecule (i.e. target molecules that have not reacted with the ligand candidate). From this, the concentration of reacted target molecule (i.e. target molecule-ligand conjugate) at that particular time point can be inferred and hence the rate of reaction between the target molecule and the ligand candidate.

As used herein, references to a "particular point in time" or "particular time point" in relation to the concentration of the "free" thiol groups in the reaction mixture or aliquot thereof, the concentration of unreacted target molecule and hence the concentration of reacted target molecule (i.e. target molecule-ligand conjugate) are to the point in time at which the reaction mixture or aliquot thereof is contacted with the thiol quantification reagent. After the reaction mixture or aliquot thereof is contacted with the thiol quantification reagent, target molecules will continue to react with ligand candidates during any incubation period. However, the thiol quantification reagent is preferably selected to react much more quickly with the target molecules than the ligand candidate, so to a first approximation any reaction between the target molecules and the ligand candidates after the addition of the thiol quantification reagent is minimal.

The rate of reaction between the target molecule and the ligand candidate can be calculated based on a single measurement of the biophysical property or based on multiple measurements, each taken following quenching at a different time point during the course of the reaction.

Where multiple measurements are used, the reaction mixture or aliquot thereof is contacted with the thiol quantification reagent at a variety of different time points measured from the point at which the reaction between the target molecule and ligand candidate begins. The person of skill in the art can select a suitable number of different time points, suitable intervals between these time points and a suitable length of time over which these time points are spread. For example, these steps might be repeated at between 1 and 10 different time points. These time points might be spread over a suitable period of time, depending on the combination of ligand candidate and target molecule used and in particular the reactivity of the ligand candidate. For example, the time points might be spread over 300 hours, 250 hours, 200 hours, 150 hours, 100 hours, 50 hours, 20 hours or 10 hours from the point at which the reaction begins. To improve accuracy, repeat measurements may be taken.

The measurements of the biophysical property can then be used to calculate the rate of reaction between the target molecule and the ligand candidate. Preferably, the measurements of the biophysical property are plotted against time. A mathematical operation may then be applied to this data, for example an exponential decay may be fitted or the first order derivative of a fitting function may be calculated. A parameter such as rate constant, half-life or the gradient of the slope at a defined time point may then be quantified. This parameter can then be used to compare the rate of reaction between different ligand candidates.

Figure 1:
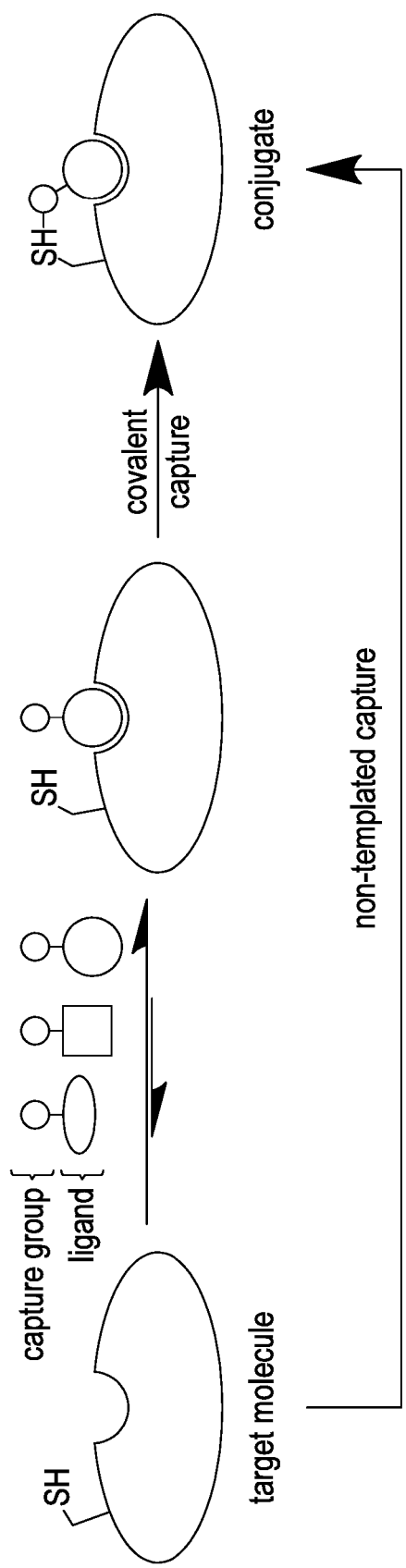
Figure 2:
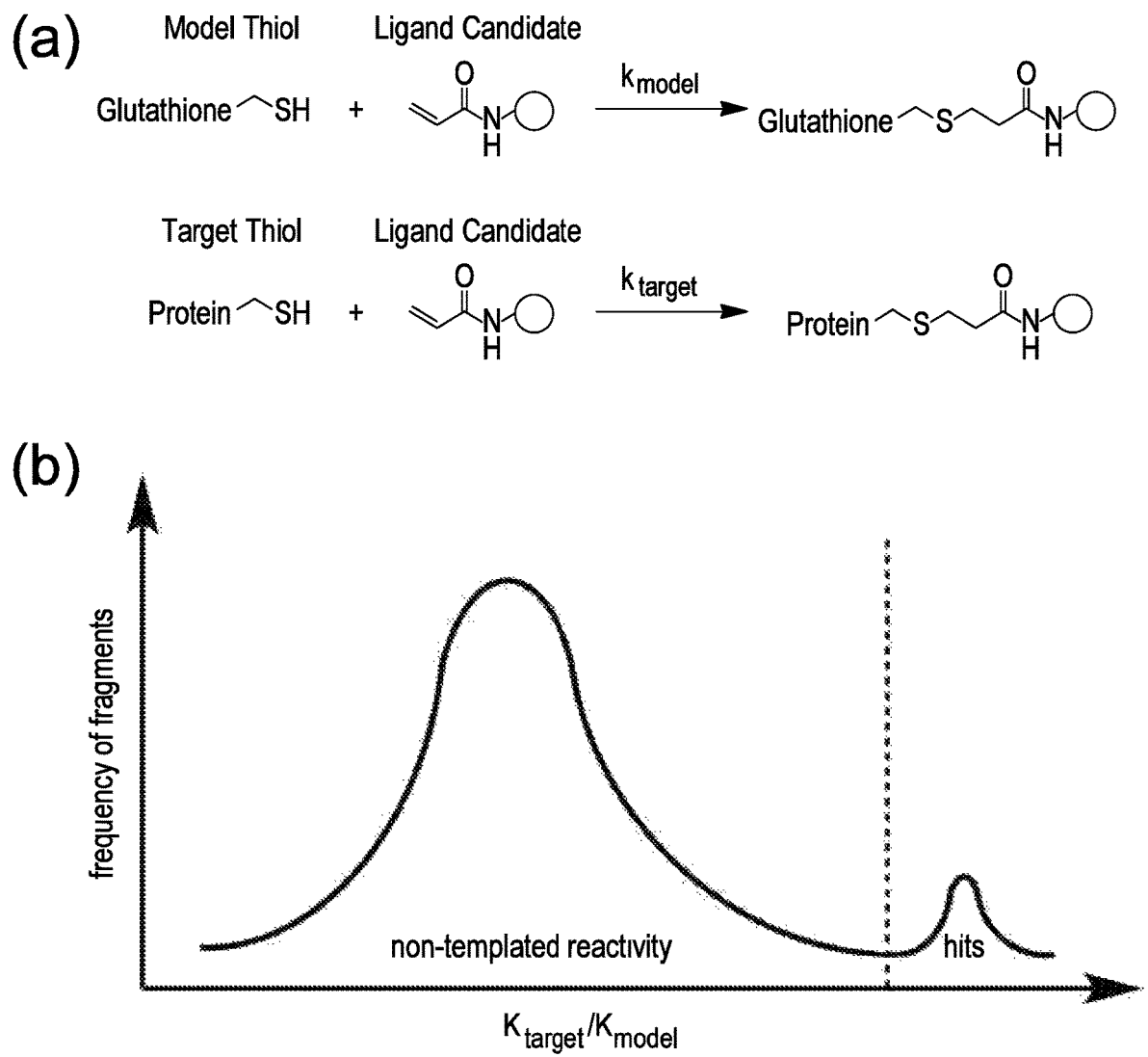
Figure 3:
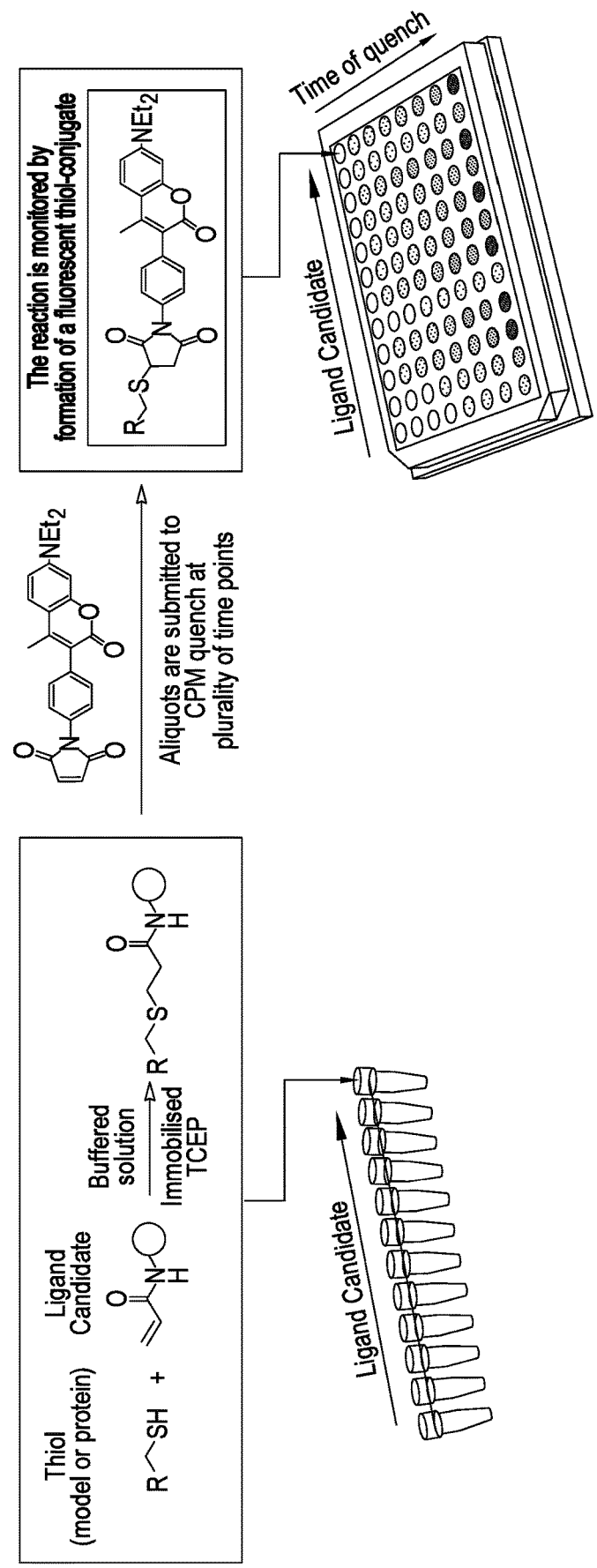
FIG. 3 is an illustration of steps in one embodiment of the method according to the first aspect of the present invention.
Figure 4:
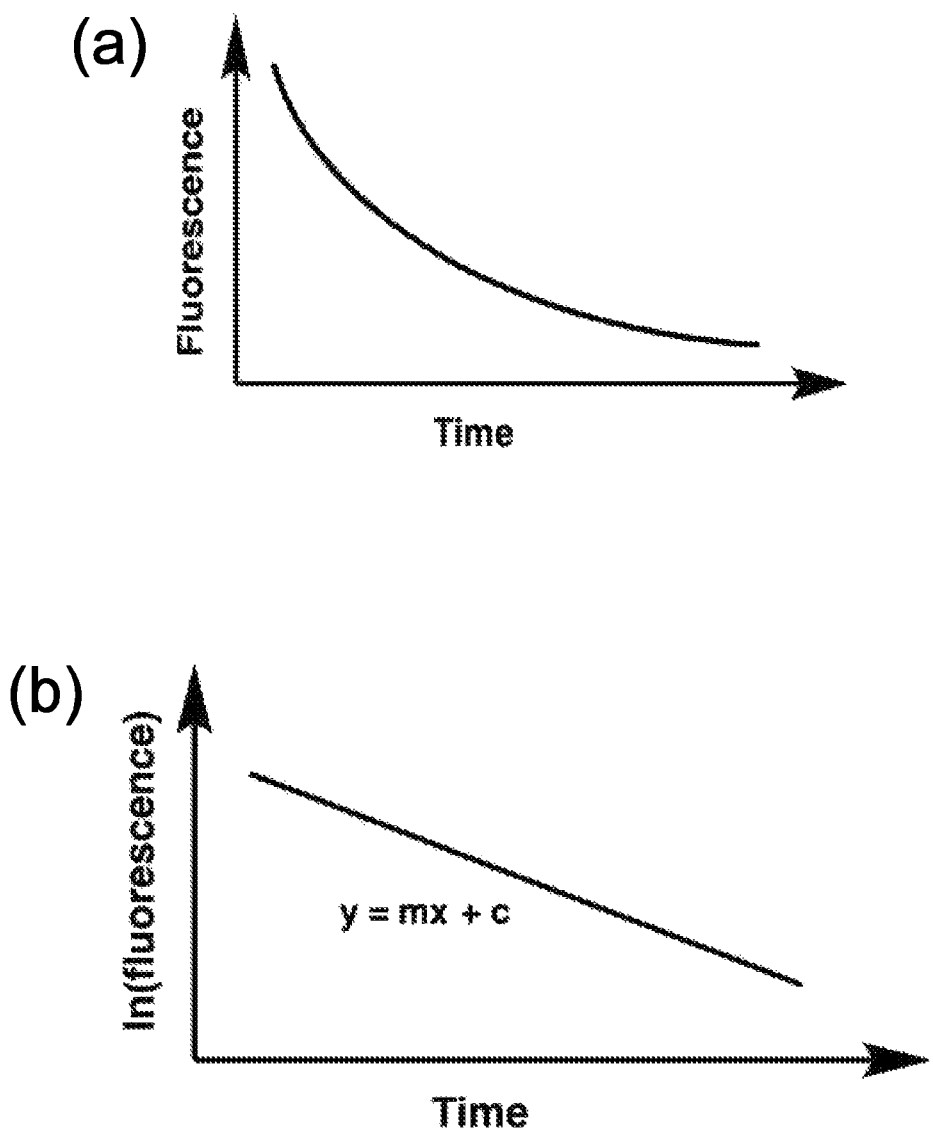
FIG. 4(a) is an exemplary plot of fluorescence over time for a given ligand candidate. Rate constants are derived by applying a first order exponential decay to the data points.
FIG. 4(b) is an exemplary plot of ln(fluorescence) over time for a given ligand candidate. Rate constants are derived by applying a linear fit to the data points.

Preferably, the measurements of the biophysical property are used to calculate a rate constant for the formation of the target molecule-ligand conjugate. This may be done using any suitable method. For example, the measurements of the biophysical property may first be plotted against time. Rate constants may then be calculated by fitting a first order exponential decay to the data, as illustrated in FIG. 4a). Alternatively, rate constants may be calculated by performing a linear fit to a plot of logarithm of biophysical property against time, as illustrated in 4b).

As mentioned above, the quenching step at each time point may involve the entire reaction mixture, a substantial proportion thereof or just an aliquot thereof. Where the entire reaction mixture or a substantial proportion thereof is quenched, the steps of providing a target molecule, contacting the target molecule with the ligand candidate, forming the target molecule-ligand conjugate, contacting the reaction mixture with the thiol quantification reagent and measuring the biophysical property of the reaction mixture (i.e. steps a) to e)) are all repeated. In each repetition, the reaction mixture is contacted with the thiol quantification reagent at a different time point during the reaction, i.e. a different amount of time following the contact of the target molecule with the ligand candidate.

The thiol quantification reagent may be added directly to the reaction mixture, for example in the container in which the target molecule was contacted with the ligand candidate. Alternatively, the entire reaction mixture (or substantially all of the reaction mixture) may be transferred into a quench plate comprising the thiol quantification reagent.

Where the entire reaction mixture or a substantial proportion thereof is quenched, a much smaller volume of the reaction mixture is generally required in step b) than when quenching aliquots of the reaction mixture, as a new reaction mixture will be formed for each repetition of the method.

If just an aliquot of the reaction mixture is transferred into the quench plate, a larger volume of the reaction mixture is generally required in step b), as an aliquot of this reaction mixture will be removed for each repetition of the method. Furthermore, it is only necessary to repeat steps d) and e). In each repetition, the aliquot of the reaction mixture is contacted with the thiol quantification reagent at a different time point during the reaction, i.e. a different amount of time following the contact of the target molecule with the ligand candidate.

One preferred embodiment of the method according to the first aspect of the invention comprises the steps of:
 a) providing a target molecule comprising a binding site of interest and a thiol group within or near the binding site of interest;
 b) contacting the target molecule with a ligand candidate in a reaction mixture, wherein the ligand candidate comprises a functional group which is capable of forming an irreversible covalent bond with said thiol group;
 c) forming an irreversible covalent bond between the thiol group of the target molecule and the functional group of the ligand candidate, thereby forming a target molecule-ligand conjugate;
 d) transferring an aliquot of the reaction mixture into a quench plate comprising a thiol quantification reagent at a first time point during the reaction, wherein the thiol quantification reagent is capable of bonding to free thiol groups to form a quantification conjugate which provides the aliquot with a biophysical property assessable by a biophysical method;
 e) measuring the biophysical property of the aliquot; and
 f) calculating the rate of reaction between the target molecule and the ligand; wherein steps d) and e) are repeated one or more further times, during which step d) is carried out at one or more further, different time points during the reaction.

The measurements of the biophysical property may be normalised against a control, for example a target molecule-only control.

Where only a single measurement of the biophysical property is take, the quenching step occurs at only a single time point during the course of the reaction. Thus, the steps of the method according to the first aspect are carried out only once for each ligand candidate.

This does not, of course, preclude the possibility that this method may be repeated for any given ligand candidate, with quenching carried out at the same time point in each repetition.

Even with only a single measurement of the biophysical property, the rate of reaction between the target molecule and the ligand can be calculated, or at least approximated.

For example, the calculation of the conversion of the target molecule to the target molecule-ligand conjugate allows for a first approximation of rate of reaction. In order to allow the calculation of the conversion of the target molecule to the target molecule-ligand conjugate from a single measurement of the biophysical property, two approximations can be made:
 1. the value of the biophysical property at a T=0 (when no target molecule-ligand conjugate has formed) is equal to the biophysical property when no ligand candidate has been introduced (equivalent to skipping steps b) and c) of the method according to the first aspect); and
 2. the value of the biophysical property when the target molecule has converted entirely to target molecule-ligand conjugate is either a) equal to the biophysical property when no target molecules has been introduced; or b) is equal to zero.

Once these two values of the biophysical property have been determined, ligand candidates can be screened using only a single measurement of the biophysical property.

The single measurement of the biophysical property may be used to approximate a rate of reaction for the formation of the target molecule-ligand conjugate, for example by relating the biophysical property measured in step e) to the conversion of the target molecule to the target molecule-ligand candidate. Specifically, if a mathematical description of the reaction is characterized, then a rate constant for the reaction can be derived. For example, where all of the reactions are carried out under pseudo-first order kinetics, it is known that the reaction will follow a one phase exponential decay.

While the use of multiple measurements of the biophysical property following quenching at multiple different time points allows more accurate analysis and comparison of the rate of reaction between different ligand candidates, the use of a single measurement of the biophysical property for each ligand candidate represents a more high-throughput technique that may be preferable under certain circumstances.

The method according to the first aspect of the present invention may further comprise the step of calculating the rate enhancement for the ligand candidate. This may comprise:
 g) repeating steps a) to f) using a model thiol instead of the target molecule, to calculate the rate of reaction between the model thiol and the ligand candidate, using the same ligand candidate; and
 h) calculating the rate enhancement for the ligand candidate by comparing the rate of reaction between the target molecule and the ligand candidate against the rate of reaction between the model thiol and the ligand candidate.

The description above of the conditions under which the target molecule is reacted with the ligand candidate, and the calculation of the rate of reaction, rate constant etc. apply mutatis mutandis to the reaction of the model thiol with the ligand candidate.

The model thiol may comprise any suitable model thiol, for example a small molecule containing a thiol group. The model thiol may comprise an amino acid derivative such as glutathione, a peptide or a protein. The model thiol may comprise a variant of the target molecule with a thiol group at a different surface position compared to the target molecule. More than one model thiol may be used, for example a small number of variants of the target molecule with thiol groups at different surface positions. Where multiple model thiols are used, for example a small number of variants of the target molecule with thiol groups at different surface positions, the average reaction rate of the variants can be calculated and used as the overall control reaction rate.

Where rate constants for the formation of the target molecule-ligand conjugate and model thiol-ligand conjugate are calculated, rate enhancement may be calculated by comparing the rate constant for the formation of the target molecule-ligand conjugate against the rate constant for the formation of the model thiol-ligand conjugate. For example, the rate enhancement for the ligand candidate may be calculated by dividing the rate constant for the formation of the target molecule-ligand conjugate by the rate constant for the formation of the model-thiol conjugate. Other suitable methods would also be known to the skilled person.

Calculating the rate enhancement for a given ligand candidate takes into account the intrinsic reactivity of the functional group. Thus, different types of functional group and more diverse scaffolds can be used in the same screen.

The rate enhancement for a ligand candidate can be used to determine whether the ligand candidate is of interest, for instance as the starting point for the development of a new drug. Such a ligand candidate is termed a "hit". The method according to the first aspect of the present invention may further comprise the step of:

i) determining whether the rate enhancement for the ligand candidate is above a chosen threshold level, wherein a ligand candidate with a rate enhancement above this threshold level is classified as a hit ligand.

A ligand candidate is usually classified as a "hit" if has a significantly enhanced rate constant compared to the model thiol.

The threshold level may be empirically determined. Because the intrinsic reactivity of the thiol residue will vary depending upon the target molecule, it is preferred that the threshold level is based on standard deviations from the mean. The threshold level may, for example, be two standard deviations over the mean or three standard deviations over the mean.

The method according to the first aspect of the invention may further comprise the step of:

j) repeating steps a) to f) with one or more further ligand candidates.

Of course, each of the plurality of ligand candidates can be subjected to steps a) to f) simultaneously or sequentially, in parallel.

Steps g) to i) may also be repeated for each ligand candidate. A ligand candidate may be defined as a "hit" in accordance with step i) after the rate enhancements for all of the plurality of ligand candidates being screened, or a subset thereof, have been calculated. This is because the range of rate enhancements for the ligand candidates may affect the threshold level above which a ligand candidate is classified as a "hit".

Additionally, since reactions between ligand candidates and target protein obey the two-step mechanism set out in FIG. 8, the observed rate constant displays the following hyperbolic dependence on ligand candidate concentration (where, [l]=concentration of ligand candidate, $k_{obs}$=observed rate constant)

$$k_{obs} = k_2[l]/(K_d+[l])$$

Therefore the assay can be used to calculate both $k_2$ and $K_d$ by experimentally determining $k_{obs}$ at a suitable range of ligand candidate concentrations. Typically $K_d$ and $k_2$ would then be determined by fitting a hyperbolic curve to a plot of $k_{obs}$ against ligand candidate concentration (FIG. 9).

Accordingly, steps a) to e) of the method according to the first aspect of the present invention may be carried out multiple times with different concentrations of the ligand candidate. The method may also comprise a further step of:

j) determining the dissociation constant for the candidate ligand

The constants $K_d$ and $k_2$ can be used to rank hit ligands either independently or in combination with the rate enhancement as discussed above.

In a further aspect, the present invention provides a method of measuring the dissociation constant between a target molecule and a ligand candidate comprising the steps of:

a) providing a target molecule comprising a binding site of interest and a thiol group within or near the binding site of interest;
b) contacting the target molecule with a ligand candidate in a reaction mixture, wherein the ligand candidate comprises a functional group which is capable of forming an irreversible covalent bond with said thiol group;
c) forming an irreversible covalent bond between the thiol group of the target molecule and the functional group of the ligand candidate, thereby forming a target molecule-ligand conjugate;
d) contacting the reaction mixture or an aliquot thereof with a thiol quantification reagent at a defined time point during the reaction, wherein the thiol quantification reagent is capable of bonding to free thiol groups to form a quantification conjugate which provides the reaction mixture or aliquot thereof with a biophysical property assessable by a biophysical method;
e) measuring the biophysical property of the reaction mixture or aliquot thereof;
f) calculating the rate of reaction between the target molecule and the ligand candidate;
g) repeating steps a) to f) with multiple different concentrations of the ligand candidate; and
h) calculating the dissociation constant between the target molecule and the ligand candidate.

Preferably, the plurality of ligand candidates comprises a library of ligand candidates. The method of the present invention allows an independent rate of reaction, rate constant and/or rate enhancement to be derived for each ligand candidate in the library.

Those of skill in the art will be familiar with various techniques that can routinely be employed to create libraries of molecules or fragments modified to comprise a functional group which is capable of covalently bonding to the thiol group in the target molecule. The library of molecules to be screened against the target molecule may be obtained in a variety of ways including, for example, through commercial and non-commercial sources, by synthesizing such compounds using standard chemical synthesis technology or combinatorial synthesis technology. For example, a suitable technique for creating a library of molecules to be screened in the method of the present invention can be found in Allen, C. E. et al.[6], which is incorporated herein by reference.

The library preferably comprises at least 25 different molecules or fragments, for example at least 100, at least 500, at least 1000, or at least 10,000 different molecules or fragments.

An exemplary library is set out in Table 1 below, in which the functional group comprises acrylamide. Additional candidates are given in Table 2, in which the functional groups include chloroacetamide, epoxide, SNAr substrates, vinyl sulfone, cyanamides and aryl nitriles.

TABLE 1

Exemplary library of ligand candidates. All solutions are 50 mM in DMSO

| Reference | Structure |
|---|---|
| CA-009 | 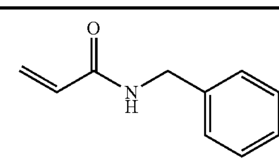 |

TABLE 1-continued
Exemplary library of ligand candidates. All solutions are 50 mM in DMSO
| Reference | Structure |
|---|---|
| CA-012 | 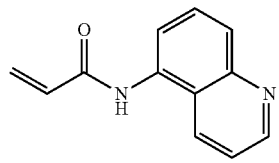 |
| CA-028 | 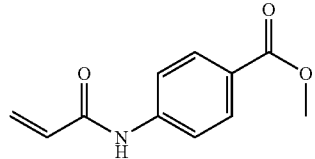 |
| CA-029 | 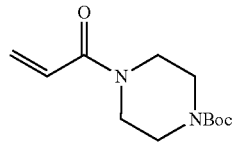 [SMILES: C=CC(=O)N1CCN(C(=O)OC(C)(C)C)CC1] |
| CA-030 | 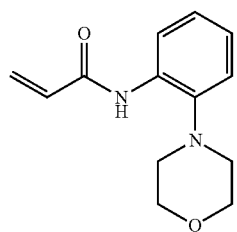 [SMILES: C=CC(=O)Nc1ccccc1N1CCOCC1] |
| CA-031 | 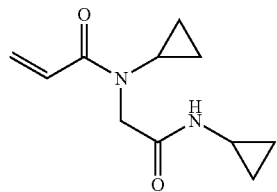 |
| CA-032 | 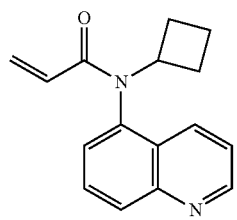 [SMILES: C=CC(=O)N(c1cccc2ncccc12)C1CCC1] |
| CA-034 | 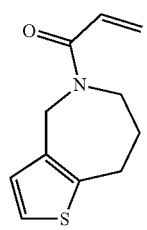 |
| CA-037 | 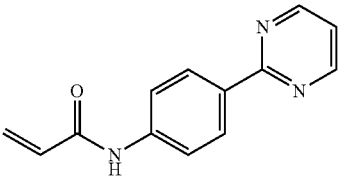 [SMILES: C=CC(=O)Nc1ccc(-c2ncccn2)cc1] |
| CA-038 | 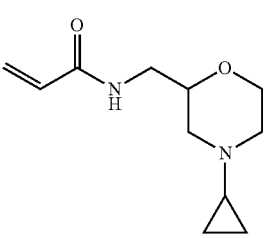 |
| CA-039 | 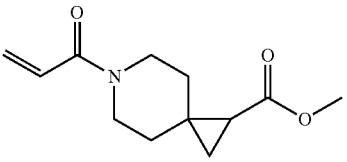 [SMILES: C=CC(=O)N1CCC2(CC1)CC2C(=O)OC] |
| CA-040 | 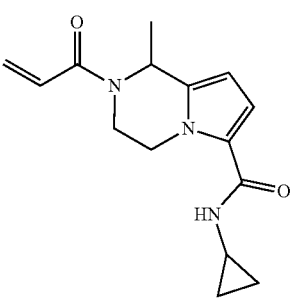 [SMILES: C=CC(=O)N1CCn2c(C(=O)NC3CC3)ccc2C1C] |
| CA-041 | 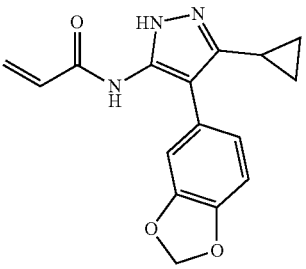 [SMILES: C=CC(=O)Nc1[nH]nc(C2CC2)c1-c1ccc2c(c1)OCO2] |
| CA-042 | 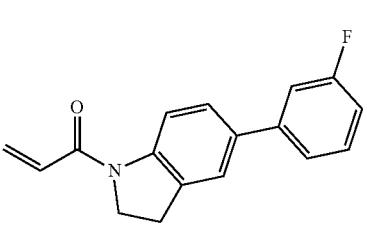 [SMILES: C=CC(=O)N1CCc2cc(-c3cccc(F)c3)ccc21] |

TABLE 1-continued
Exemplary library of ligand candidates. All solutions are 50 mM in DMSO
| Reference | Structure |
|---|---|
| CA-044 | 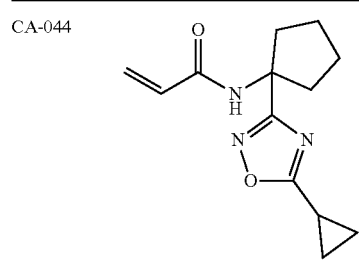 |
| CA-046 | 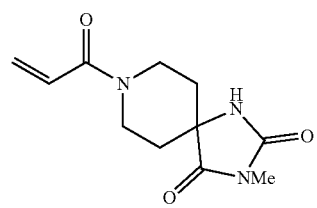 [SMILES: C=CC(=O)N1CCC2(CC1)NC(=O)N(C)C2=O] |
| CA-047 | 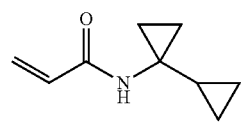 |
| CA-048 | 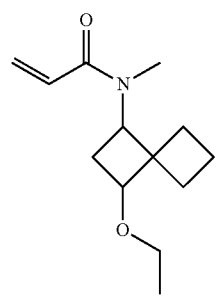 [SMILES: C=CC(=O)N(C)C1CC(OCC)C12CCC2] |
| CA-054 | 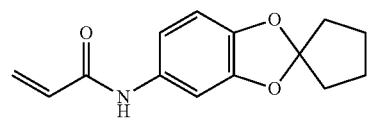 [SMILES: C=CC(=O)Nc1ccc2c(c1)OC1(CCCC1)O2] |
| CA-055 | 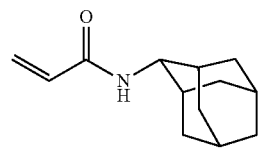 |
| CA-056 | 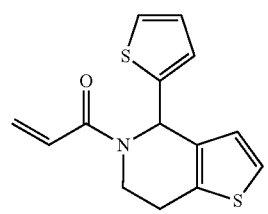 [SMILES: C=CC(=O)N1CCc2sccc2C1c1cccs1] |
| CA-057 | 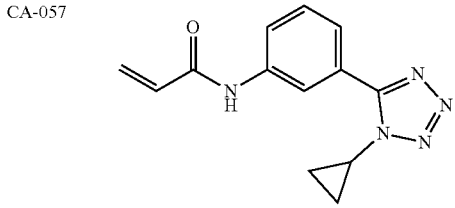 |
| CA-060 | 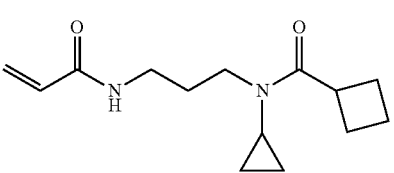 [SMILES: C=CC(=O)NCCCN(C(=O)C1CCC1)C1CC1] |
| CA-072 | 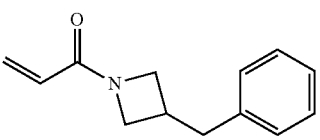 |
| CA-079 | 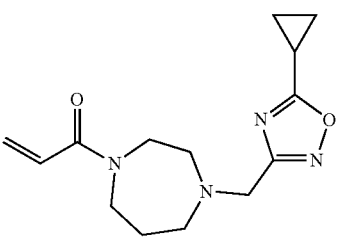 [SMILES: C=CC(=O)N1CCCN(Cc2noc(C3CC3)n2)CC1] |
| CA-080 | 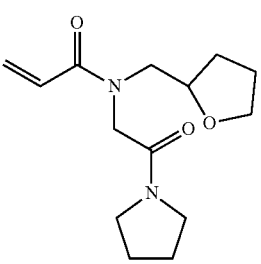 [SMILES: C=CC(=O)N(CC(=O)N1CCCC1)CC1CCCO1] |
| CA-081 | 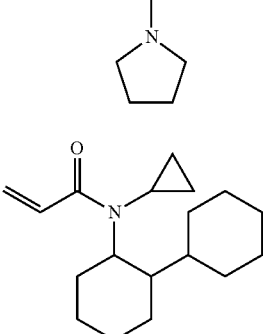 |
| CA-084 | 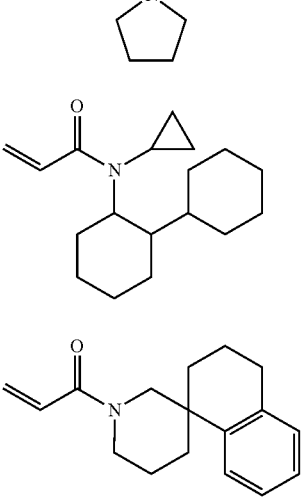 |

TABLE 1-continued
Exemplary library of ligand candidates. All solutions are 50 mM in DMSO
| Reference | Structure |
|---|---|
| CA-087 | 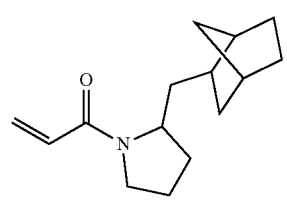 [SMILES: C=CC(=O)N1CCCC1CC1CC2CCC1C2] |
| CA-088 | 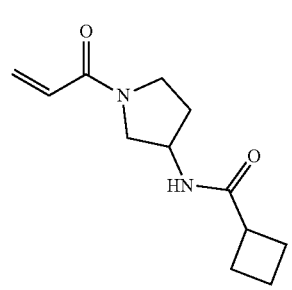 [SMILES: C=CC(=O)N1CCC(NC(=O)C2CCC2)C1] |
| CA-089 | 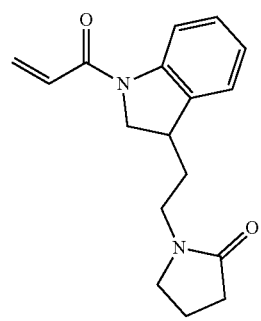 [SMILES: C=CC(=O)N1CC(CCN2CCCC2=O)c2ccccc21] |
| CA-091/238 | 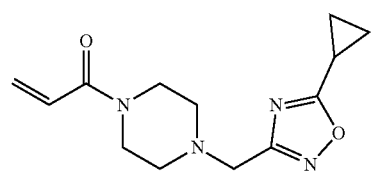 [SMILES: C=CC(=O)N1CCN(Cc2noc(C3CC3)n2)CC1] |
| CA-092 | 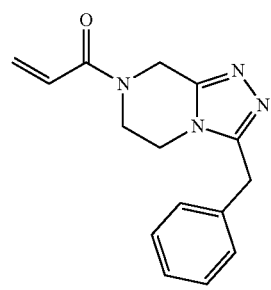 [SMILES: C=CC(=O)N1CCn2c(Cc3ccccc3)nnc2C1] |
| CA-093 | 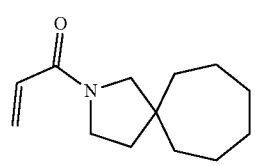 |
| CA-096 | 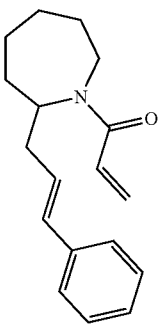 [SMILES: C=CC(=O)N1CCCCCC1C/C=C/c1ccccc1] |
| CA-097 | 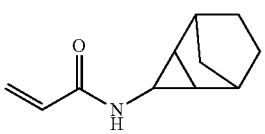 |
| CA-098 | 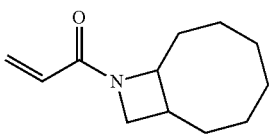 |
| CA-099 | 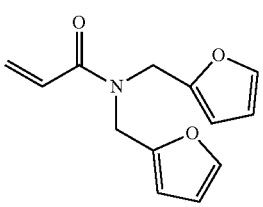 [SMILES: C=CC(=O)N(Cc1ccco1)Cc1ccco1] |
| CA-129 | 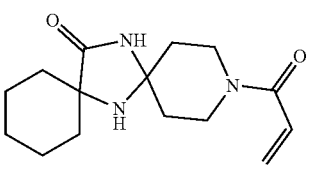 [SMILES: C=CC(=O)N1CCC2(CC1)NC(=O)C1(CCCCC1)N2] |
| CA-141 | 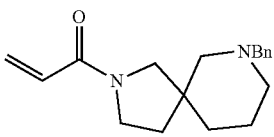 [SMILES: C=CC(=O)N1CCC2(CCCN(Cc3ccccc3)C2)C1] |
| CA-142 | 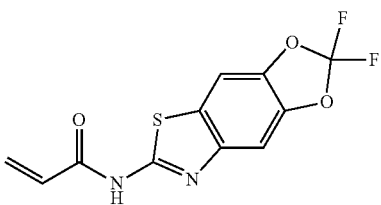 [SMILES: C=CC(=O)Nc1nc2cc3c(cc2s1)OC(F)(F)O3] |
| CA-143 | 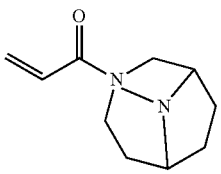 |

TABLE 1-continued
Exemplary library of ligand candidates. All solutions are 50 mM in DMSO
| Reference | Structure |
|---|---|
| CA-144 | 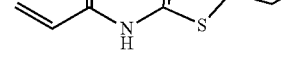 |
| CA-145 | 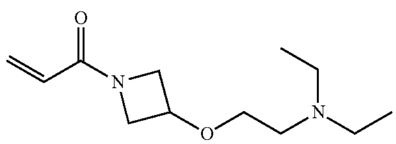 [SMILES: C=CC(=O)N1CC(OCCN(CC)CC)C1] |
| CA-155 | 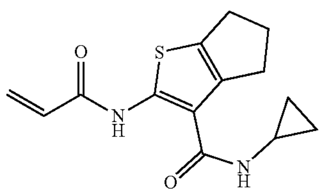 [SMILES: C=CC(=O)Nc1sc2c(c1C(=O)NC1CC1)CCC2] |
| CA-157 | 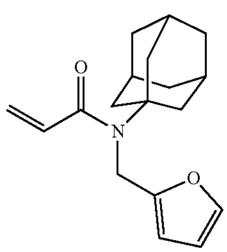 [SMILES: C=CC(=O)N(Cc1ccco1)C12CC3CC(CC(C3)C1)C2] |
| CA-159 | 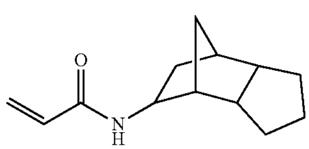 |
| CA-162 | 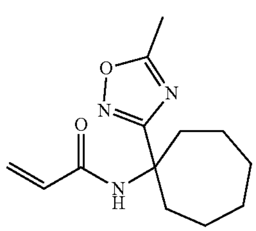 [SMILES: C=CC(=O)NC1(c2noc(C)n2)CCCCCC1] |
| CA-167 | 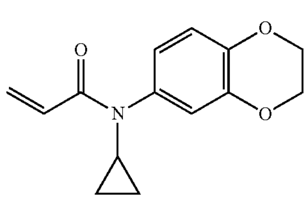 [SMILES: C=CC(=O)N(c1ccc2c(c1)OCCO2)C1CC1] |
| CA-170 |  |
| CA-171 | |
| CA-173 | |
| CA-179 | |
| CA-178 | |
| CA-182 | |

TABLE 1-continued

Exemplary library of ligand candidates. All solutions are 50 mM in DMSO

| Reference | Structure |
|---|---|
| CA-184 | 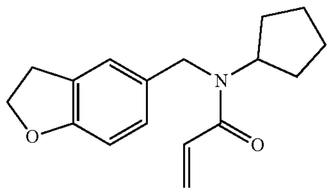 [SMILES: C=CC(=O)N(Cc1ccc2c(c1)CCO2)C1CCCC1] |
| CA-187 | 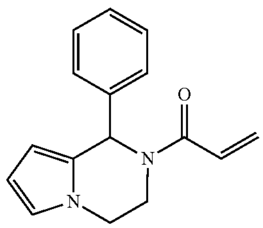 [SMILES: C=CC(=O)N1CCn2cccc2C1c1ccccc1] |
| CA-190 | 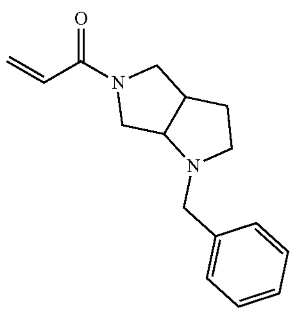 [SMILES: C=CC(=O)N1CC2CCN(Cc3ccccc3)C2C1] |
| CA-193 | 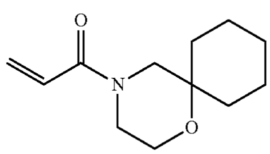 |
| CA-194 | 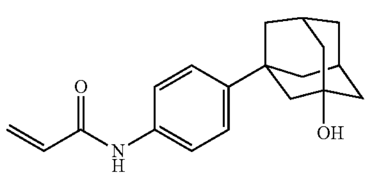 [SMILES: C=CC(=O)Nc1ccc(C23CC4CC(CC(O)(C4)C2)C3)cc1] |
| CA-196 | 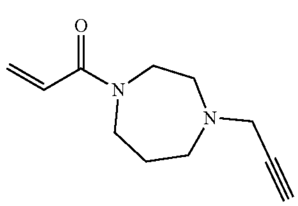 |
| CA-202 | 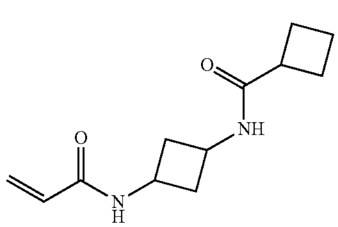 [SMILES: C=CC(=O)NC1CC(NC(=O)C2CCC2)C1] |
| CA-203 | |
| CA-207 | |
| CA-211 | |
| CA-218 | |
| CA-219 | |
| EL-1004 | |
| EL-1007 | |

TABLE 1-continued
Exemplary library of ligand candidates. All solutions are 50 mM in DMSO
| Reference | Structure |
|---|---|
| EL-1012 | 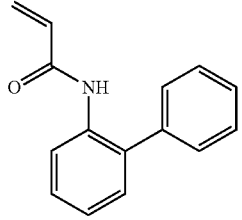 [SMILES: C=CC(=O)Nc1ccccc1-c1ccccc1] |
| EL-1050 | 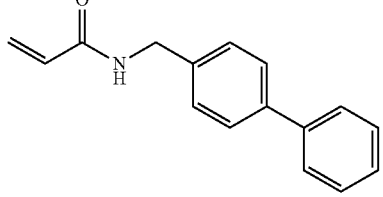 |
| EL-1051 | 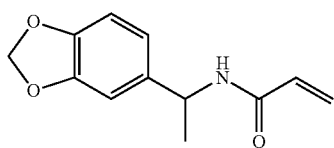 [SMILES: C=CC(=O)NC(C)c1ccc2c(c1)OCO2] |
| EL-1059 | 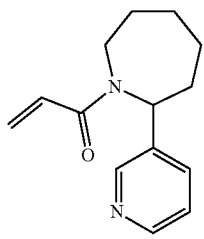 [SMILES: C=CC(=O)N1CCCCCC1c1cccnc1] |
| EL-1062 | 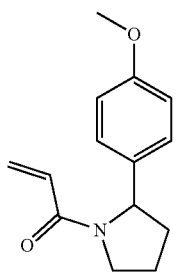 [SMILES: C=CC(=O)N1CCCC1c1ccc(OC)cc1] |
| EL-1063 | 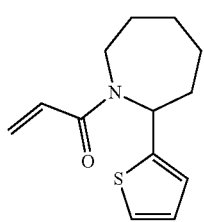 [SMILES: C=CC(=O)N1CCCCCC1c1cccs1] |
| EL-1064 | 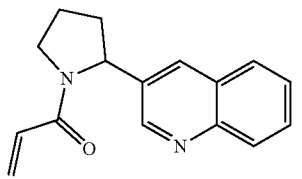 [SMILES: C=CC(=O)N1CCCC1c1cnc2ccccc2c1] |
| EL-1071 | 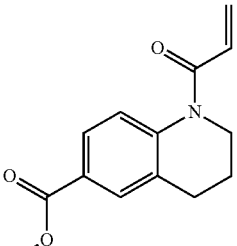 |
| EL-1074 | 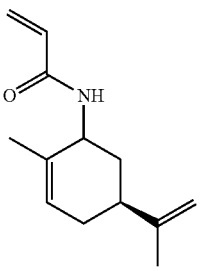 |
| EL-1083 | 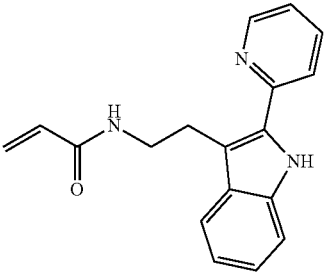 [SMILES: C=CC(=O)NCCc1c(-c2ccccn2)[nH]c2ccccc12] |
| EL-1084 | 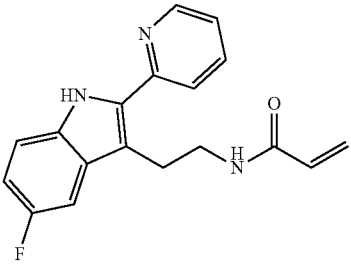 [SMILES: C=CC(=O)NCCc1c(-c2ccccn2)[nH]c2ccc(F)cc12] |
| EL-1098 | 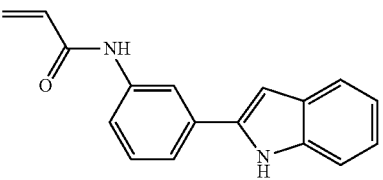 [SMILES: C=CC(=O)Nc1cccc(-c2cc3ccccc3[nH]2)c1] |
| EL-1101 | 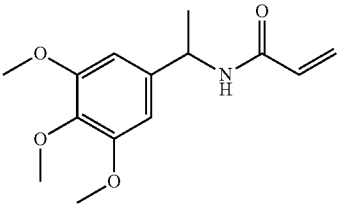 [SMILES: C=CC(=O)NC(C)c1cc(OC)c(OC)c(OC)c1] |

TABLE 1-continued

Exemplary library of ligand candidates. All solutions are 50 mM in DMSO

| Reference | Structure |
|---|---|
| EL-1109 | |
| EL-1114 | |
| EL-1121 | |
| EL-1140 | |
| EL-1134 | |
| EL-1143 | 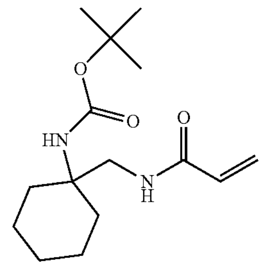 [SMILES: C=CC(=O)NCC1(NC(=O)OC(C)(C)C)CCCCC1] |
| EL-1152 | 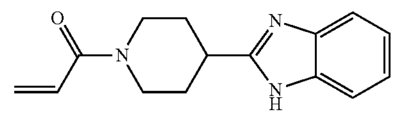 [SMILES: C=CC(=O)N1CCC(c2nc3ccccc3[nH]2)CC1] |
| EL-1153 | 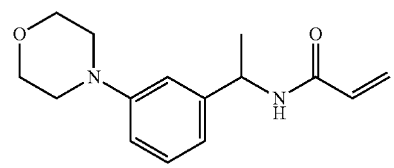 [SMILES: C=CC(=O)NC(C)c1cccc(N2CCOCC2)c1] |
| EL-1155 | 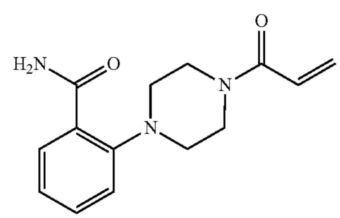 [SMILES: C=CC(=O)N1CCN(c2ccccc2C(N)=O)CC1] |
| EL-1156 | 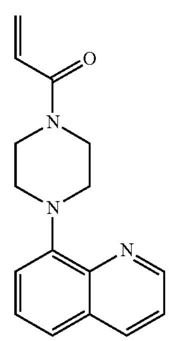 [SMILES: C=CC(=O)N1CCN(c2cccc3cccnc23)CC1] |
| EL-1157 | 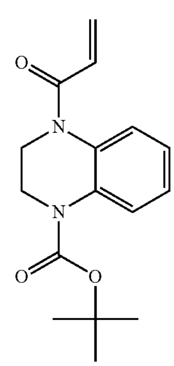 [SMILES: C=CC(=O)N1CCN(C(=O)OC(C)(C)C)c2ccccc21] |

TABLE 1-continued

Exemplary library of ligand candidates. All solutions are 50 mM in DMSO

| Reference | Structure |
|---|---|
| EL-1160 | 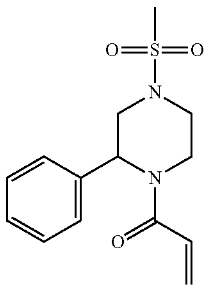 [SMILES: C=CC(=O)N1CCN(S(C)(=O)=O)CC1c1ccccc1] |
| EL-1164 | 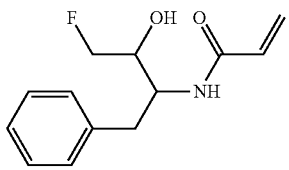 [SMILES: C=CC(=O)NC(Cc1ccccc1)C(O)CF] |
| EL-1168 | 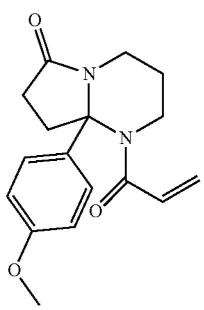 [SMILES: C=CC(=O)N1CCCN2C(=O)CCC12c1ccc(OC)cc1] |
| EL-1170 | 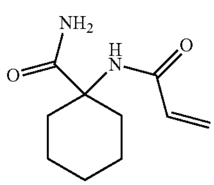 |
| EL-1178 | 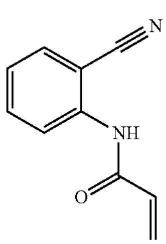 |
| EL-1183 | 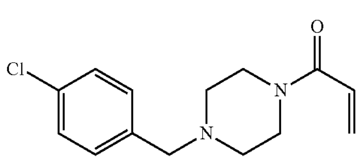 [SMILES: C=CC(=O)N1CCN(Cc2ccc(Cl)cc2)CC1] |
| EL-1187 | 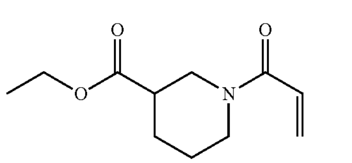 |
| EL-1174 | |
| CA-236 | |
| BN-62 | |
| BN-346 | |
| BN-80 | |
| GC-248 | |
| CA-053 | |

TABLE 1-continued
Exemplary library of ligand candidates. All solutions are 50 mM in DMSO
| Reference | Structure |
|---|---|
| CA-106 | 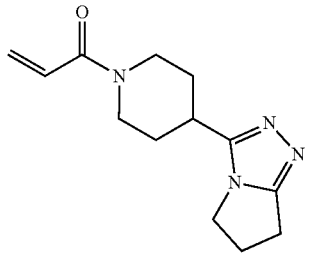 [SMILES: C=CC(=O)N1CCC(c2nnc3n2CCC3)CC1] |
| CA-118 | 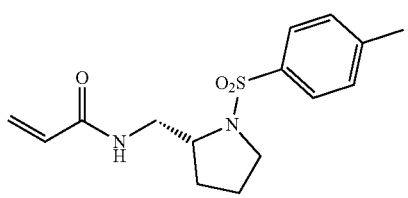 |
| CA-152 | 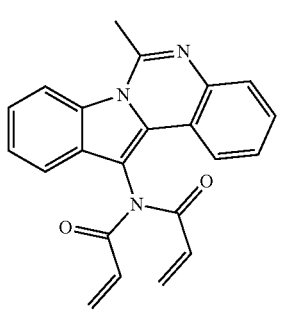 [SMILES: C=CC(=O)N(C(=O)C=C)c1c2ccccc2n2c(C)nc3ccccc3c12] |
| CA-165-1 | 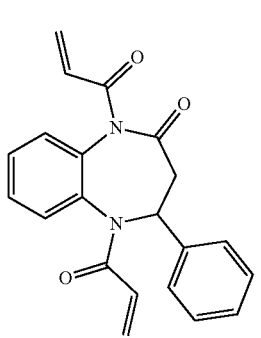 [SMILES: C=CC(=O)N1C(=O)CC(c2ccccc2)N(C(=O)C=C)c2ccccc21] |
| CA-188 | 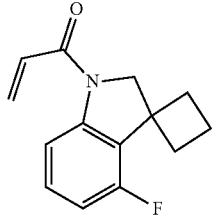 [SMILES: C=CC(=O)N1CC2(CCC2)c2c(F)cccc21] |
| CA-192 | 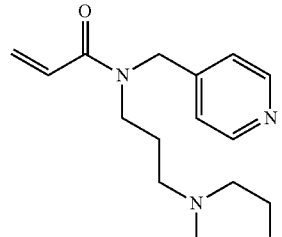 |
| CA-216 | 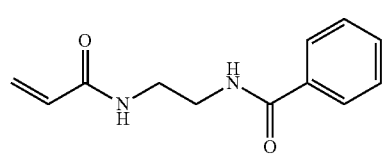 [SMILES: C=CC(=O)NCCNC(=O)c1ccccc1] |
| CA-224 | 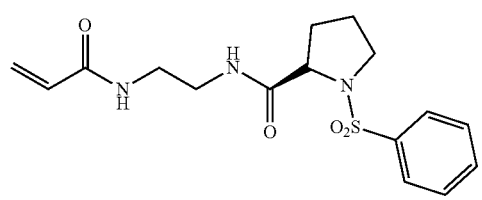 |
| BN63 | 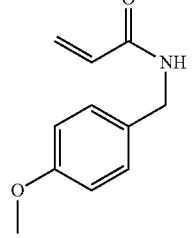 |
| BN62 | 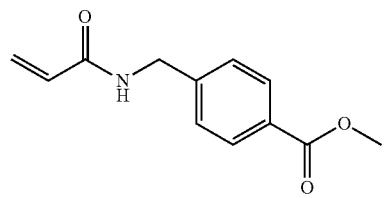 [SMILES: C=CC(=O)NCc1ccc(C(=O)OC)cc1] |
| BN66 | 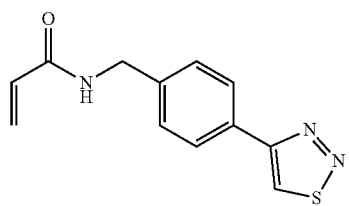 [SMILES: C=CC(=O)NCc1ccc(-c2csnn2)cc1] |
| BN78 | 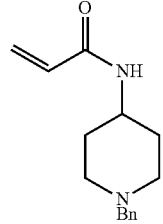 [SMILES: C=CC(=O)NC1CCN(Cc2ccccc2)CC1] |

TABLE 1-continued

Exemplary library of ligand candidates. All solutions are 50 mM in DMSO

| Reference | Structure |
|---|---|
| BN122 | 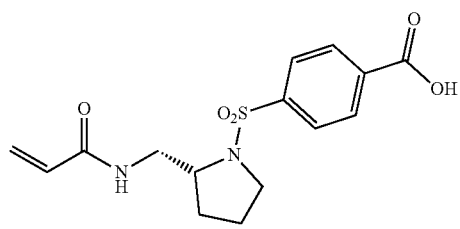 |

TABLE 2

Additional exemplary ligand candidates. All solutions are 50 mM in DMSO

| | |
|---|---|
| EN-01 | 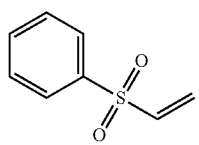 |
| EN-02 | 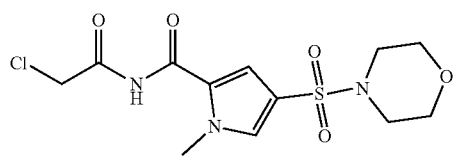 [SMILES: Cn1cc(S(=O)(=O)N2CCOCC2)cc1C(=O)NC(=O)CCl] |
| EN-03 | 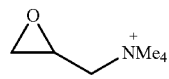 |
| EN-04 | 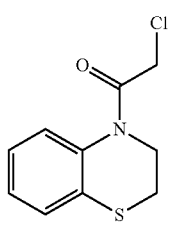 [SMILES: O=C(CCl)N1CCSc2ccccc21] |
| EN-05 | 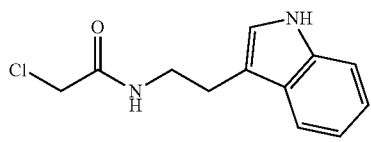 [SMILES: O=C(CCl)NCCc1c[nH]c2ccccc12] |
| EN-06 | 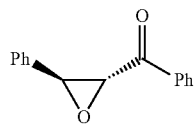 [SMILES: O=C(c1ccccc1)[C@@H]1O[C@H]1c1ccccc1] |
| EN-07 | 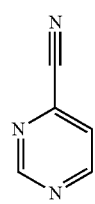 |

TABLE 2-continued

Additional exemplary ligand candidates. All solutions are 50 mM in DMSO

| | |
|---|---|
| EN-08 | 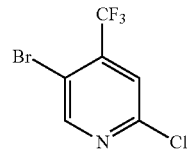 [SMILES: FC(F)(F)c1cc(Cl)ncc1Br] |
| EN-09 | 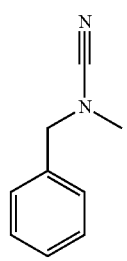 |
| EN-10 | 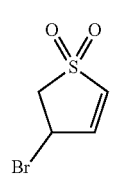 |
| EN-11 | 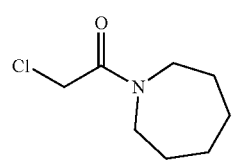 [SMILES: O=C(CCl)N1CCCCCC1] |
| EN-12 | 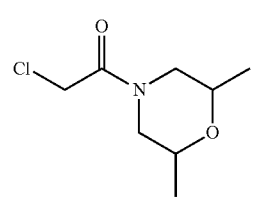 |

The exact reaction conditions for screening a library of ligand candidates against the target molecule comprising the thiol group will be dependent upon factors such as the chemical nature of the chosen library and can be determined by the skilled person in an empirical manner.

The method according to the first aspect of the present invention may further comprise the step of:

k) developing a hit ligand into a drug or other inhibitor.

Where the thiol group is endogenous to the target molecule, the hit ligand may be developed into an irreversible covalent inhibitor. Alternatively, the hit ligand may be modified into a non-covalent analogue (for example by removal of the functional group) and developed into a reversible inhibitor.

Where the target molecule has been modified to comprise the thiol group, the hit ligand may be modified into a non-covalent analogue (for example by removal of the functional group) and developed into a reversible inhibitor.

Where the hit ligand comprises a fragment, this fragment can be elaborated through, for example, fragment linking, fragment growing, combining with other molecules or combining with one another to provide high-affinity drug leads. New fragments can be merged with elements from known inhibitors to produce new, high-affinity inhibitors.

The development of the hit ligand may comprise one or more of the following steps:

obtaining structures of the ligand bound to the target molecule, for example by X-ray crystallography or NMR;

fragment elaboration conducted according to standard medicinal chemistry techniques;

repetition of the method according to the first aspect of the present invention using analogues of the hit ligand to select for higher affinity ligand candidates;

use of mass spectrometry or NMR to confirm protein modification and to identify the residue of modification;

conducting other biochemical assays on the hits and derivatives thereof in parallel, for example to check for protein inhibition (where the target molecule is Cdk2, these other biochemical assays might include a cyclin binding assay and/or a kinase activity assay)

Ligands identified according to the methods of the present invention find use, for example, as novel therapeutic drug lead compounds, enzyme inhibitors, probes for biochemical assays or protein crosslinking agents and the like.

Exemplary embodiments of the method according to the first aspect of the present invention are illustrated in FIGS. 1, 2, 3 and 4.

A second aspect of the present invention provides a hit ligand or ligand candidate identified according to the method of the first aspect of the present invention.

The second aspect of the present invention therefore includes any of the ligand candidates set out in Table 1 above, if identified as hit ligands using the method according to the first aspect of the present invention.

The second aspect of the present invention also encompasses derivatives of such ligands. Derivatives may include various aromatic or aliphatic substitutions, such as any halogen, any atom except H, any alkyl chain, any cycle, any carbocycle or any heterocycle. Additionally, other electrophilic groups may be used in place of the acrylamide functionality, for example acrylate, α,β-unsaturated ketones, vinyl sulfonamides, vinylsulfone, vinylsulfonate, α-halogenated ketones, epoxides and substituted derivatives thereof.

Example 1 describes the screening of a library of 120 acrylamides against wild type cyclin-dependent kinase 2 (Cdk2) which contains one endogenous surface exposed cysteine (C177) residue, using glutathione as a model thiol. This method identified two "hit ligands"; CA-184 and EL-1071, the structures of which are set out below:

CA-184:

(A)

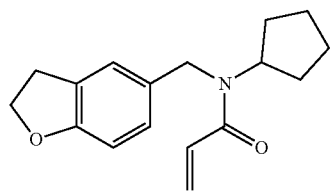

EL-1071:

-continued (B)

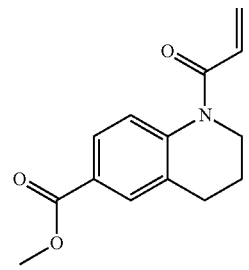

Example 2 describes the screening of a library of 120 acrylamides against wild type cyclin-dependent kinase 2 (Cdk2) which contains one endogenous surface exposed cysteine (C177) residue. In this example, mutant Cdk2 (C177A, F80C, K278C) containing two engineered surface exposed cysteine residues was used as a model thiol. This method identified two "hit ligands"; CA-89 and CA-92, the structures of which are set out below:

CA-89:

(C)

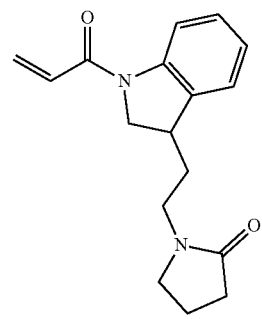

CA-92:

(D)

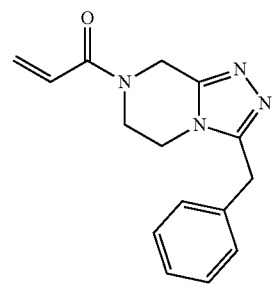

The second aspect of the present invention therefore includes CA-184 (Formula A), CA-89 (Formula C) and CA-92 (Formula D), which are novel fragments created by the present inventors and identified as hit ligands using the method according to the first aspect of the present invention.

The second aspect of the present invention also encompasses derivatives of CA-184 (Formula A), CA-89 (Formula C) and CA-92 (Formula D), as defined above. The second aspect of the present invention therefore includes compounds of the following formulae and derivatives thereof, wherein R comprises any suitable electrophilic group, for example an electrophilic group selected from the group consisting of acrylamide functionalities, acrylate, α,β-unsaturated ketones, vinyl sulfonamides, vinylsulfone, vinylsulfonate, α-halogenated ketones, epoxides and substituted derivatives thereof:

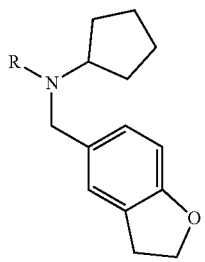

(I)

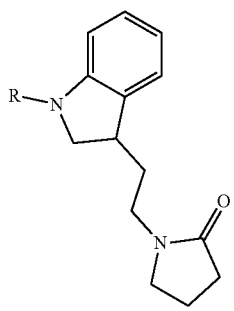

(II)

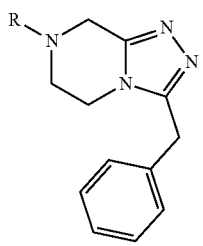

(III)

As discussed above, derivatives of these compounds may include various aromatic or aliphatic substitutions, such as any halogen, any atom except H, any alkyl chain, any cycle, any carbocycle or any heterocycle.

A third aspect of the present invention provides a drug developed using the method according to the first aspect of the invention.

The third aspect of the present invention therefore includes a drug developed from any of the ligand candidates set out in Table 1 above, if identified as hit ligands using the method according to the first aspect of the present invention, and derivatives thereof.

Thus, for example, the third aspect of the present invention comprises a drug developed from any of the "hit ligands" discussed above, such as those of Formula I, Formula II and Formula III, including CA-184 (Formula A), CA-89 (Formula C) or CA-92 (Formula D) or derivatives thereof, as defined above.

The third aspect of the present invention also comprises a drug developed from EL-1071 (Formula B) or derivatives thereof, for example those of Formula IV, wherein R comprises any suitable electrophilic group, for example an electrophilic group selected from the group consisting of acrylamide functionalities, acrylate, α,β-unsaturated ketones, vinyl sulfonamides, vinylsulfone, vinylsulfonate, α-halogenated ketones, epoxides and substituted derivatives thereof:

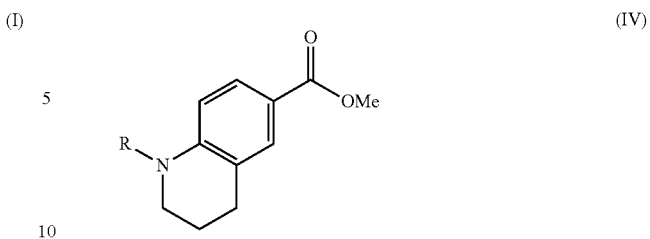

(IV)

As discussed above, derivatives of these compounds may include various aromatic or aliphatic substitutions, such as any halogen, any atom except H, any alkyl chain, any cycle, any carbocycle or any heterocycle.

The kinetic thiol consumption assay discussed above also has potential uses outside the context of the method according to the first aspect of the invention. A fourth aspect of the invention therefore provides a method of measuring the rate of reaction between a thiol and a molecule capable of reacting with said thiol comprising the steps of:

a) contacting a thiol with a molecule capable of reacting with said thiol to form a reaction product in a reaction mixture;

b) contacting the reaction mixture or an aliquot thereof with a thiol quantification reagent at a defined time point during the reaction, wherein the thiol quantification reagent is capable of bonding to free thiol groups to form a quantification conjugate which provides the reaction mixture or aliquot thereof with a biophysical property assessable by a biophysical method;

c) measuring the biophysical property of the reaction mixture or aliquot thereof; and d) calculating the rate of reaction between the thiol and the molecule capable of reacting with said thiol.

All of the details of the first aspect of the invention apply mutatis mutandis to the fourth aspect of the invention.

Thus, step b) of the fourth aspect of the invention may comprise contacting an aliquot of the reaction mixture with the thiol quantification reagent, wherein steps b) and c) are repeated one or more further times, and wherein, during each repetition, step b) is carried out at one or more further, different time points during the reaction.

Step b) of the fourth aspect of the invention may alternatively comprise contacting the entire reaction mixture or a substantial proportion thereof with the thiol quantification reagent, wherein steps a) to c) are repeated one or more further times, and wherein, during each repetition, step b) is carried out at one or more further, different time points during the reaction.

In either case, step d) may comprise calculating a rate constant for the formation of the reaction product.

Step b) may alternatively be carried out at a single time point during the reaction and step d) may comprise calculating the conversion of the thiol to the reaction product at that time point. This method may further comprise calculating an approximation of a rate constant for the formation of the reaction product.

One preferred embodiment of the method according to the fourth aspect of the invention comprises the steps of:

a) contacting a thiol with the molecule capable of reacting with said thiol to form a reaction product in a reaction mixture;

b) transferring an aliquot of the reaction mixture into a quench plate comprising a thiol quantification reagent at a defined time point during the reaction, wherein the thiol quantification reagent is capable of bonding to free thiol groups to form a quantification conjugate which provides the aliquot with a biophysical property assessable by a biophysical method;
c) measuring the biophysical property of the aliquot; and
d) calculating the rate of reaction between the thiol and the molecule capable of reacting with said thiol;
wherein steps b) and c) are repeated one or more further times, during which step b) is carried out at one or more further, different time points during the reaction.

As described above, the method according to the fourth aspect of the present invention may be used in the method according to the first aspect of the present invention, to allow the rate of reaction between a target molecule and a ligand candidate to be measured. However, the method according to the fourth aspect of the present invention may have other uses. For example, it may be used in enzymatic assays, particularly in relation to enzymes which act on thiol groups or require thiol groups.

Another preferred embodiment of the method of the fourth aspect may involve the use of a thiol quantification reagent that engages the thiol irreversibly. The meaning of irreversibly binding in this context will be understood by the skilled person, but is intended to mean that once bound to the thiol the thiol quantification reagent does not become unbound under the conditions used in the method. Such agents include but are not limited to maleimides (including but not limited to N-(7-dimethylamino-4-methylcoumarin-3-yl)maleimide and fuorescein-5-maleimide), compound 5a disclosed in Hong et al 2009[7] and 3-(7-Hydroxy-2-oxo-2H-chromen-3-ylcarbamoyl)acrylic acid methylester[8]. The use of an irreversible reagent may provide a more accurate measurement. Thiol detection reagents are discussed in more detail in Chen et al. 2010[9].

Still a further preferred embodiment of the method of the fourth aspect involves the use of a reducing agent to prevent unwanted thiol oxidation. The reducing agent is separated from the thiol prior to thiol quantification, leading to more accurate quantification of the rate of reaction. The removal of the reducing agent may be achieved by using an immobilised reducing agent, which may be added in parallel with the molecule capable of reacting with said thiol. The immobilised reducing agent can then be separated from the thiol prior to thiol quantification. Thus, in a preferred embodiment of the method of the fourth aspect, in step a) the thiol is contacted with a reducing agent in parallel with the molecule capable of reacting with said thiol, said reducing agent being removed in step b) prior to the reaction mixture or an aliquot thereof being contacted with a thiol quantification reagent.

A preferred immobilised reducing agent is tris(2-carboxyethyl)phosphine (TCEP) immobilised on agarose beads (commercially available from Thermo Fisher). TCEP could also be immobilised in other ways, which will be apparent to the skilled person (see for example Alzahrani & Welham 2014[10]). Other disulfide reducing agents (e.g phosphines and thiols) could be immobilised and used in a similar way.

The details of the invention provided in the description above and in the examples below apply mutatis mutandis to all aspects and embodiments of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The aspects of the present invention will now be illustrated by way of the following, non-limiting examples.

Examples 1 and 2

Methodology:

A library of 120 acrylamides was screened against a) human cyclin-dependent kinase 2 (Cdk2, which contains one surface exposed cysteine residue—C177), prepared by cloning cDNA into the pRSETA bacterial expression vector to generate a poly-histidine tagged Cdk2 fusion that was purified from E. coli using standard techniques, and b) a model thiol (specific details are given below). The structures of these 120 acrylamides are set out in Table 1, above.

To wells containing 150 µL thiol (Cdk2 or model thiol) (5 µM) in degassed phosphate buffer (pH 8) was added immobilized TCEP beads (2% v/v). After incubation at 4° C. for 1 hour to ensure the thiol was fully reduced, acrylamide stock solutions in DMSO were added to give a final concentration of 500 µM ligand.

At time intervals, ranging from 0.25-250 hours, 3 µL aliquots were removed (without transferring any TCEP beads) and quenched into separate fluorescence plates, in which each well contained 27 µL of CPM (1.25 µM final concentration) in degassed phosphate buffer (pH 7.5).

After incubation of the fluorescence plates for 1 hour at room temperature, fluorescence measurements (excitation/emission of 380/470 nm) were taken on a PerkinElmer EnVision multilabel plate reader and processed with EnVision Workstation version 1.12.

Fluorescence measurements were normalized against a DMSO/thiol only control and plotted against time.

Rate constants were calculated using GraphPad software Prism version 6 by fitting a first order exponential decay to the data. The rate constant for each acrylamide with Cdk2 was divided by the rate constant for that fragment with the model thiol to provide the rate enhancement for each ligand candidate.

Example 1

The model thiol in Example 1 is glutathione (GSH). The results are shown in Table 3, below. Hits were defined as fragments where $k_{Cdk2}/k_{GSH}>5.8$ (empirically determined as 3 standard deviations over the mean).

The normalised rate distribution graph is shown in FIG. 5. As can be seen from this figure, two hit fragments were identified, corresponding to CA-184 and EL-1071, the structures of which are set out below:

CA-184:

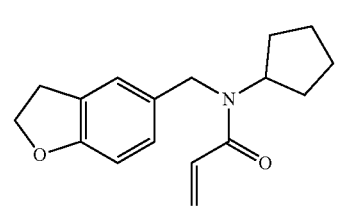

(A)

EL-1071:

41
-continued (B)
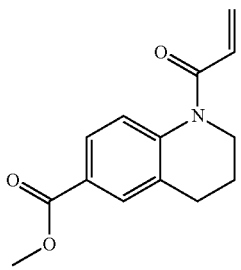

Two exemplary compounds, a negative compound EL-1007 and a hit fragment EL-1071, will be considered in more detail below by way of illustration.

As illustrated in FIGS. 6(a) and (b), the rate constant for the formation of the EL-1007-GSH conjugate ($k_{GSH}$) was 0.025, while the rate constant for the formation of the EL-1007-Cdk2 conjugate ($K_{Cdk2}$) was 0.035. Dividing the rate constant for the formation of the EL-1007-Cdk2 conjugate ($K_{Cdk2}$) by the rate constant for the formation of the EL-1007-GSH conjugate ($k_{GSH}$) gives a rate enhancement for EL-1007 of 1.4. This is below the chosen threshold rate enhancement of 5.8 and hence EL-1007 was defined as a negative compound.

As illustrated in FIGS. 7(a) and (b), the rate constant for the formation of the EL-1071-GSH conjugate ($k_{GSH}$) was 0.051, while the rate constant for the formation of the EL-1071-Cdk2 conjugate ($K_{Cdk2}$) was 0.433. Dividing the rate constant for the formation of the EL-1071-Cdk2 conjugate ($K_{Cdk2}$) by the rate constant for the formation of the EL-1071-GSH conjugate ($k_{GSH}$) gives a rate enhancement for EL-1071 of 8.5. This is above the chosen threshold rate enhancement of 5.8 and hence EL-1071 was defined as a hit fragment.

Example 2

The model thiol used in Example 2 is a mutant form of human Cdk2 (C177A, F80C, K278C) which contains two engineered surface exposed cysteine residues. Mutations were introduced by site-directed mutagenesis and the resulting cDNA was cloned into the pRSETA bacterial expression vector to generate a poly-histidine tagged Cdk2 fusion that was purified from *E. coli* using standard techniques. The results are shown in Table 3, below.

The following ligand candidates (CA-89 and CA-92) were identified as hits as they show significant rate enhancement against both model thiols (GSH and mutant Cdk2). The structures of the hits are set out below.

CA-89:

(C)
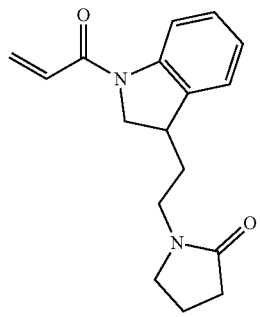

CA-92:

(D)
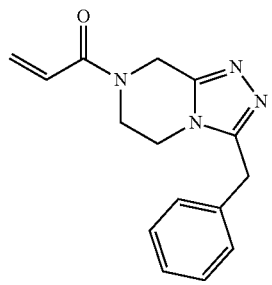

Results:

The rate constant with glutathione (k(GSH)), rate constant with Cdk2 (k(Cdk2)), rate constant with Cdk2[C177A, F80C, K278C] (k(Cdk2_mut)), and the rate enhancements calculated for each ligand candidate screened (k(Cdk2)/k(GSH) and k(Cdk2)/k(Cdk2_mut)) are set out in Table 3, below.

TABLE 3

Rate constants and rate enhancement for each ligand candidate screened

| Ligand | Rate constant with glutathione (k(GSH)) | Rate constant with Cdk2 (k(Cdk2)) | Rate constant with Cdk2[C177A, F80C, K278C] (k(Cdk2_mut)) | k(Cdk2)/ k(GSH) | k(Cdk2)/ k(Cdk2_mut) |
|---|---|---|---|---|---|
| CA-009 | 0.00469 | 0.00446 | 0.00402 | 0.94969 | 1.10766 |
| CA-012 | 0.05132 | 0.09635 | 0.41570 | 1.87744 | 0.23178 |
| CA-028 | 0.05986 | 0.17330 | 0.31380 | 2.89509 | 0.55226 |
| CA-029 | 0.01716 | 0.00892 | 0.00615 | 0.51964 | 1.44968 |
| CA-030 | 0.01590 | 0.01069 | 0.03859 | 0.67233 | 0.27701 |
| CA-031 | 0.01687 | 0.00688 | 0.00466 | 0.40806 | 1.47852 |
| CA-032 | 0.01642 | 0.02299 | 0.01104 | 1.40012 | 2.08243 |
| CA-034 | 0.01354 | 0.02784 | 0.00997 | 2.05613 | 2.79350 |
| CA-037 | 0.01523 | 0.05015 | 0.19520 | 3.29284 | 0.25692 |
| CA-038 | 0.00650 | 0.00332 | 0.00345 | 0.51015 | 0.96228 |
| CA-039 | 0.00141 | 0.00187 | 0.00304 | 1.32670 | 0.61549 |
| CA-040 | 0.03530 | 0.02965 | 0.03020 | 0.83994 | 0.98179 |
| CA-041 | 0.54410 | 1.14600 | 1.93300 | 2.10623 | 0.59286 |
| CA-042 | 0.00825 | 0.04257 | 0.13510 | 5.15750 | 0.31510 |
| CA-044 | 0.00557 | 0.00269 | 0.00154 | 0.48375 | 1.74935 |
| CA-046 | 0.00955 | 0.00343 | 0.00249 | 0.35934 | 1.37736 |

TABLE 3-continued

Rate constants and rate enhancement for each ligand candidate screened

| Ligand | Rate constant with glutathione (k(GSH)) | Rate constant with Cdk2 (k(Cdk2)) | Rate constant with Cdk2[C177A, F80C, K278C] (k(Cdk2_mut)) | k(Cdk2)/ k(GSH) | k(Cdk2)/ k(Cdk2_mut) |
|---|---|---|---|---|---|
| CA-047 | 0.00756 | 0.00560 | 0.00346 | 0.74074 | 1.61710 |
| CA-048 | 0.01364 | 0.01116 | 0.00791 | 0.81818 | 1.41034 |
| CA-054 | 0.00434 | 0.00267 | 0.04027 | 0.61400 | 0.06620 |
| CA-055 | 0.00243 | 0.00070 | 0.00101 | 0.28813 | 0.69367 |
| CA-056 | 0.01740 | 0.02004 | 0.13610 | 1.15172 | 0.14724 |
| CA-057 | 0.02585 | 0.07160 | 0.09413 | 2.76983 | 0.76065 |
| CA-060 | 0.00283 | 0.00226 | 0.00223 | 0.79880 | 1.01346 |
| CA-072 | 0.01236 | 0.02410 | 0.00481 | 1.94984 | 5.01561 |
| CA-079 | 0.00593 | 0.00553 | 0.00210 | 0.93285 | 2.63411 |
| CA-080 | 0.00706 | 0.00195 | — | 0.27638 | — |
| CA-081 | 0.00172 | 0.00879 | 0.00475 | 5.10756 | 1.85103 |
| CA-084 | 0.01002 | 0.00872 | 0.00438 | 0.87006 | 1.98859 |
| CA-087 | 0.00510 | 0.00508 | — | 0.99569 | — |
| CA-088 | 0.01352 | 0.00595 | 0.00177 | 0.43987 | 3.36559 |
| CA-089 | 0.04608 | 0.20340 | 0.02054 | 4.41406 | 9.90263 |
| CA-091 | 0.00525 | 0.00230 | — | 0.43757 | — |
| CA-092 | 0.08170 | 0.26340 | 0.01236 | 3.22399 | 21.31068 |
| CA-093 | 0.00740 | 0.00196 | 0.00507 | 0.26510 | 0.38729 |
| CA-096 | 0.01134 | 0.00340 | 0.01283 | 0.30009 | 0.26524 |
| CA-097 | 0.00533 | 0.00152 | 0.00407 | 0.28545 | 0.37346 |
| CA-098 | 0.01614 | 0.01499 | 0.00546 | 0.92875 | 2.74542 |
| CA-099 | 0.23000 | 0.28990 | 0.01590 | 1.26043 | 18.23270 |
| CA-129 | 0.00771 | 0.00274 | 0.00208 | 0.35533 | 1.31716 |
| CA-141 | 0.01384 | 0.00693 | 0.00257 | 0.50094 | 2.69347 |
| CA-142 | 0.02031 | 0.03086 | 0.02268 | 1.51945 | 1.36077 |
| CA-143 | 0.02930 | 0.01115 | 0.00505 | 0.38055 | 2.20661 |
| CA-144 | 0.04140 | 0.04682 | 0.01242 | 1.13092 | 3.76973 |
| CA-145 | 0.00318 | 0.00205 | — | 0.64248 | — |
| CA-155 | 0.26780 | 0.74300 | 1.39100 | 2.77446 | 0.53415 |
| CA-157 | 0.00399 | 0.00288 | — | 0.72335 | — |
| CA-159 | 0.00418 | 0.00232 | 0.00130 | 0.55468 | 1.78996 |
| CA-162 | 0.02564 | 0.02529 | 0.00171 | 0.98635 | 14.75496 |
| CA-167 | 0.01009 | 0.01101 | 0.00264 | 1.09118 | 4.17678 |
| CA-170 | 0.06955 | 0.29720 | 0.91970 | 4.27318 | 0.32315 |
| CA-171 | 0.00416 | 0.00423 | 0.00127 | 1.01755 | 3.34281 |
| CA-173 | 0.01577 | 0.00754 | 0.00504 | 0.47793 | 1.49544 |
| CA-179 | 0.00683 | 0.00760 | 0.00719 | 1.11243 | 1.05644 |
| CA-178 | 0.14150 | 0.15070 | 0.61070 | 1.06502 | 0.24677 |
| CA-182 | 0.00304 | 0.00381 | — | 1.25444 | — |
| CA-184 | 0.01856 | 0.22350 | 0.07366 | 12.04203 | 3.03421 |
| CA-187 | 0.04403 | 0.02811 | 0.01772 | 0.63843 | 1.58634 |
| CA-190 | 0.01268 | 0.00347 | 0.00305 | 0.27350 | 1.13630 |
| CA-193 | 0.02378 | 0.02444 | 0.01059 | 1.02775 | 2.30784 |
| CA-194 | 0.00306 | 0.00505 | 0.01393 | 1.65054 | 0.36246 |
| CA-196 | 0.00365 | 0.00372 | — | 1.02056 | — |
| CA-202 | 0.00506 | 0.00543 | 0.00132 | 1.07374 | 4.11439 |
| CA-203 | 0.01382 | 0.04586 | 0.07903 | 3.31838 | 0.58029 |
| CA-207 | 0.00972 | 0.00578 | 0.00111 | 0.59465 | 5.21861 |
| CA-211 | 0.00538 | 0.00368 | 0.00172 | 0.68395 | 2.14386 |
| CA-218 | 0.01290 | 0.03272 | 0.11920 | 2.53643 | 0.27450 |
| CA-219 | 0.06515 | 0.23170 | 0.71880 | 3.55641 | 0.32234 |
| EL-1004 | 0.01818 | 0.06444 | 0.19230 | 3.54455 | 0.33510 |
| EL-1007 | 0.02461 | 0.03473 | 0.05859 | 1.41121 | 0.59276 |
| EL-1012 | 0.00837 | 0.00519 | 0.03512 | 0.62036 | 0.14786 |
| EL-1050 | 0.00204 | 0.00166 | 0.00126 | 0.81296 | 1.31742 |
| EL-1051 | 0.00461 | 0.00298 | 0.00361 | 0.64636 | 0.82508 |
| EL-1059 | 0.00656 | 0.00213 | 0.00449 | 0.32444 | 0.47382 |
| EL-1062 | 0.00509 | 0.00448 | 0.00663 | 0.88023 | 0.67617 |
| EL-1063 | 0.00353 | 0.00274 | 0.00461 | 0.77749 | 0.59553 |
| EL-1064 | 0.01205 | 0.00589 | 0.00766 | 0.48896 | 0.76909 |
| EL-1071 | 0.05049 | 0.43300 | 0.32300 | 8.57596 | 1.34056 |
| EL-1074 | 0.00876 | 0.00300 | 0.00342 | 0.34208 | 0.87734 |
| EL-1083 | 0.00618 | 0.00098 | 0.00284 | 0.15827 | 0.34461 |
| EL-1084 | 0.00286 | 0.00314 | 0.00599 | 1.10123 | 0.52470 |
| EL-1098 | 0.01147 | 0.01063 | 0.03487 | 0.92677 | 0.30485 |
| EL-1101 | 0.00780 | 0.00341 | 0.00226 | 0.43725 | 1.50996 |
| EL-1109 | 0.00862 | 0.00827 | 0.00922 | 0.95950 | 0.89656 |
| EL-1114 | 0.02997 | 0.07947 | 0.22990 | 2.65165 | 0.34567 |
| EL-1121 | 0.02567 | 0.01328 | 0.01555 | 0.51734 | 0.85402 |
| EL-1140 | 0.00797 | 0.00303 | 0.00407 | 0.38057 | 0.74551 |
| EL-1134 | 0.00444 | 0.00710 | 0.02097 | 1.59743 | 0.33853 |
| EL-1143 | 0.00493 | 0.01400 | 0.00802 | 2.83918 | 1.74607 |

TABLE 3-continued

Rate constants and rate enhancement for each ligand candidate screened

| Ligand | Rate constant with glutathione (k(GSH)) | Rate constant with Cdk2 (k(Cdk2)) | Rate constant with Cdk2[C177A, F80C, K278C] (k(Cdk2_mut)) | k(Cdk2)/ k(GSH) | k(Cdk2)/ k(Cdk2_mut) |
|---|---|---|---|---|---|
| EL-1152 | 0.00606 | 0.00612 | 0.00580 | 1.00891 | 1.05501 |
| EL-1153 | 0.00284 | 0.00103 | 0.00419 | 0.36187 | 0.24487 |
| EL-1155 | 0.00836 | 0.00466 | 0.00382 | 0.55755 | 1.22117 |
| EL-1156 | 0.01763 | 0.01873 | 0.02157 | 1.06239 | 0.86834 |
| EL-1157 | 0.12600 | 0.20060 | 0.30460 | 1.59206 | 0.65857 |
| EL-1160 | 0.02860 | 0.01181 | 0.00414 | 0.41294 | 2.85404 |
| EL-1164 | 0.00485 | 0.00239 | 0.00073 | 0.49340 | 3.26155 |
| EL-1168 | 0.01343 | 0.00974 | 0.00175 | 0.72494 | 5.55074 |
| EL-1170 | 0.00243 | 0.00308 | — | 1.27052 | — |
| EL-1178 | 0.04788 | 0.16110 | 0.16500 | 3.36466 | 0.97636 |
| EL-1183 | 0.00676 | 0.00376 | 0.00864 | 0.55643 | 0.43532 |
| EL-1187 | 0.00634 | 0.00596 | 0.00336 | 0.93943 | 1.77420 |
| EL-1174 | 0.00253 | 0.00090 | 0.00688 | 0.35547 | 0.13095 |
| CA-236 | 0.00506 | 0.00116 | 0.00395 | 0.22855 | 0.29244 |
| BN-62 | 0.00157 | 0.00190 | 0.00167 | 1.21315 | 1.13628 |
| BN-346 | 0.00299 | 0.00428 | 0.00146 | 1.42948 | 2.92145 |
| BN-80 | 0.02984 | 0.04190 | 0.12840 | 1.40416 | 0.32632 |
| GC248 | 0.01495 | 0.01014 | 0.01560 | 0.67826 | 0.65000 |
| CA-53 | 0.00428 | 0.00097 | 0.00547 | 0.22599 | 0.17704 |
| CA-106 | 0.00227 | 0.00145 | 0.00151 | 0.63672 | 0.95762 |
| CA-118 | 0.00280 | 0.00698 | 0.00415 | 2.49090 | 1.68242 |
| CA-152 | 0.25010 | 0.83580 | 3.05900 | 3.34186 | 0.27323 |
| CA-165-1 | 0.44440 | 0.39450 | 1.13600 | 0.88771 | 0.34727 |
| CA-188 | 0.19030 | 0.55000 | 1.16100 | 2.89017 | 0.47373 |
| CA-192 | 0.00676 | 0.00341 | 0.00447 | 0.50481 | 0.76252 |
| CA216 | 0.00254 | 0.00676 | 0.01899 | 2.66037 | 0.35598 |
| CA-224 | 0.00508 | 0.00155 | 0.00358 | 0.30454 | 0.43289 |
| BN-63 | 0.00215 | 0.00194 | 0.00330 | 0.90111 | 0.58818 |
| BN-65 | 0.00292 | 0.00121 | 0.00398 | 0.41344 | 0.30309 |
| BN-66 | 0.00160 | 0.00089 | 0.00350 | 0.55648 | 0.25413 |
| BN-78 | 0.00403 | 0.00116 | 0.00196 | 0.28734 | 0.59052 |
| BN122 | 0.00283 | 0.00219 | 0.00117 | 0.77530 | 1.87907 |

Example 3

A further set of set of additional Cdk2 mutants were screened, all containing the C177A mutation and therefore with only one cysteine on the surface:

F80C (without the K278C mutation)
H71C
S276C
N272
T182C
R122C
S181C

Mutations were introduced by site-directed mutagenesis and the resulting cDNA was cloned into the pRSETA bacterial expression vector to generate a poly-histidine tagged Cdk2 fusion that was purified from *E. coli* using standard techniques.

The data from this screen are shown in Tables 4 and 5.

TABLE 4

Rate constants for each ligand with each mutant Cdk2

| Ligand name | Glutathione | Cdk2 | Cdk2 | Cdk2 | Cdk2 | Cdk2 | Cdk2 | Cdk2 | Cdk2 |
|---|---|---|---|---|---|---|---|---|---|
| | | | Cysteine position | | | | | | |
| | NA | WT | F80C | H71C | S276C | N272C | T182C | R122C | S181C |
| | | | Additional mutations | | | | | | |
| | — | — | C177A | C177A | C177A | C177A | C177A | C177A | C177A |
| CA-009 | 0.006985 | 0.01679 | 0.003513 | 0.001981 | 0.005718 | 0.009206 | 0.1507 | 0.004047 | 0.003288 |
| CA-012 | 0.05195 | 0.09635 | 0.202 | 0.01647 | 0.05118 | 0.02176 | 0.3013 | 0.03583 | 0.1301 |
| CA-028 | 0.06113 | 0.1733 | 0.07185 | 0.06327 | 0.06356 | 0.04653 | 0.3207 | 0.02124 | 0.03097 |
| CA-029 | 0.0211 | 0.008917 | 0.002607 | 0.002672 | 0.006904 | 0.005738 | 0.03726 | 0.004289 | 0.006959 |
| CA-030 | 0.01673 | 0.01069 | 0.025 | 0.002204 | 0.004445 | 0.00403 | 0.009966 | 0.004845 | 0.01251 |
| CA-031 | 0.0174 | 0.003072 | 0.0005005 | | 0.009212 | 0.02034 | 0.01849 | 0.003846 | 0.009769 |
| CA-032/228 | 0.01636 | 0.02299 | 0.03651 | 0.2513 | 0.03029 | 0.04919 | 0.2422 | 0.02509 | 0.01707 |
| CA-034 | 0.01847 | 0.01944 | 0.02361 | 0.03232 | 0.0502 | 0.01334 | 0.1874 | 0.01185 | 0.01082 |
| CA-037 | 0.01516 | 0.05015 | 0.964 | 0.02977 | 0.02673 | 0.02636 | 0.1865 | 0.0147 | 0.02267 |
| CA-038 | 0.01131 | 0.005901 | | 0.009335 | 0.006591 | 0.006696 | 0.01973 | 0.004175 | 0.005333 |
| CA-039 | 0.002035 | 0.0005702 | | | 0.002319 | 0.001526 | 0.0029 | 0.001809 | 0.001289 |

TABLE 4-continued

Rate constants for each ligand with each mutant Cdk2

| | Glutathione | Cdk2 | Cdk2 | Cdk2 | Cdk2 | Cdk2 | Cdk2 | Cdk2 | Cdk2 |
|---|---|---|---|---|---|---|---|---|---|
| | | | | | Cysteine position | | | | |
| | NA | WT | F80C | H71C | S276C | N272C | T182C | R122C | S181C |
| Ligand name | | — | C177A | C177A | C177A | C177A | C177A | C177A | C177A |
| CA-040/230 | 0.04288 | 0.02965 | 0.0133 | 0.03145 | 0.03282 | 0.1319 | 0.05436 | 0.01222 | 0.01059 |
| CA-041 | 0.5506 | 1.146 | | 0.003968 | 0.003524 | 0.004727 | 0.471 | 0.002178 | 0.003169 |
| CA-042 | 0.01463 | 0.04257 | 0.006272 | 0.007409 | 0.008245 | 0.001395 | 0.08115 | 0.001778 | 0.004663 |
| CA-044 | 0.008146 | 0.002694 | | | 0.0009087 | | 0.002365 | 0.001875 | 0.0009239 |
| CA-046 | 0.01631 | 0.003432 | 0.001897 | 0.00116 | 0.01153 | 0.001516 | 0.009705 | 0.00391 | 0.00324 |
| CA-047 | 0.0123 | 0.0056 | 0.001607 | | 0.006721 | 0.002048 | 0.01308 | 0.003233 | 0.003402 |
| CA-048 | 0.01891 | 0.01346 | 0.01517 | 0.004408 | 0.01473 | 0.01029 | 0.05001 | 0.003826 | 0.0114 |
| CA-054 | 0.004326 | 0.002666 | 0.006411 | 0.004426 | 0.004109 | 0.005397 | 0.004582 | 0.001816 | 0.002032 |
| CA-055 | 0.002381 | 0.0009681 | | 0.001157 | 0.00116 | 0.01093 | 0.0006241 | 0.001021 | 0.002556 |
| CA-056 | 0.01742 | 0.02004 | 0.08682 | 0.02185 | 0.03094 | 0.02696 | 0.3197 | 0.01362 | 0.03604 |
| CA-057 | 0.02651 | 0.0716 | 0.05671 | 0.04338 | 0.04258 | 0.07649 | 0.4908 | 0.03118 | 0.02834 |
| CA-060 | 0.005138 | 0.00367 | ~0.0004944 | | 0.005711 | 0.01889 | 0.00832 | 0.002402 | 0.004014 |
| CA-072 | 0.02221 | 0.0241 | 0.0057 | 0.3655 | 0.08965 | 0.2085 | 0.1492 | 0.00778 | 0.04813 |
| CA-079 | 0.009223 | 0.00939 | 0.001299 | 0.002765 | 0.006132 | 0.004534 | 0.007716 | 0.004453 | 0.04575 |
| CA-080/239 | 0.01204 | 0.00279 | 0.001007 | | 0.003474 | 0.003318 | 0.01162 | 0.002083 | 0.001658 |
| CA-081/240 | 0.002337 | 0.01776 | 0.0108 | 0.002113 | 0.01732 | 0.007657 | 0.01943 | 0.001659 | 0.02322 |
| CA-084 | 0.01681 | 0.008718 | 0.03044 | 0.0138 | 0.01813 | 0.001146 | 0.06469 | 0.004528 | 0.007158 |
| CA-087 | 0.00846 | 0.00896 | 0.004048 | 0.3006 | 0.006194 | 0.002576 | 0.05469 | 0.002699 | 0.005463 |
| CA-088 | 0.01947 | 0.005947 | 0.002347 | | 0.008557 | 0.01092 | 0.01771 | 0.009119 | 0.003708 |
| CA-089 | 0.04691 | 0.2034 | 0.08953 | 0.163 | 0.1436 | 0.2038 | 0.784 | 0.02168 | 0.02699 |
| CA-091/238 | 0.007745 | 0.002299 | 0.0007964 | 0.001506 | 0.007277 | 0.002919 | 0.01551 | 0.005358 | 0.008821 |
| CA-092 | 0.08356 | 0.2634 | 0.008842 | 0.2247 | 0.5455 | 0.5985 | 0.5417 | 0.1896 | 0.07642 |
| CA-093 | 0.01326 | 0.003412 | 0.01686 | 0.007628 | 0.0176 | 0.005578 | 0.05399 | 0.004124 | 0.01029 |
| CA-096/146 | 0.01125 | 0.003401 | 0.01846 | 0.01 | 0.01436 | 0.01002 | 0.1161 | 0.008035 | 0.1459 |
| CA-097 | 0.009838 | 0.001519 | 0.001856 | 0.001541 | 0.008009 | 0.005802 | 0.01424 | 0.003442 | |
| CA-098 | 0.02562 | 0.0242 | 0.01519 | 0.0205 | 0.08188 | 0.1716 | 0.1221 | 0.008918 | 0.02273 |
| CA-099/153 | 0.2123 | 0.2899 | 0.03506 | 0.06172 | 0.481 | 0.5081 | 0.4326 | 0.5145 | 0.314 |
| CA-129/235 | 0.01093 | 0.002741 | 0.001988 | 0.0003575 | 0.01838 | 0.004302 | 0.009647 | 0.01011 | 0.002434 |
| CA-141 | 0.01802 | 0.006933 | 0.001715 | | | 0.004517 | 0.009235 | 0.0043 | 0.003487 |
| CA-142 | 0.02028 | 0.03086 | 0.1954 | 0.003644 | 0.07463 | 0.006229 | 0.2609 | 0.002674 | 0.00817 |
| CA-143 | 0.02932 | 0.01115 | 0.002972 | 0.002353 | 0.0186 | 0.01449 | 0.06917 | 0.006009 | 0.002691 |
| CA-144 | 0.04163 | 0.04682 | 0.02063 | 0.3437 | 0.05252 | 0.08909 | 0.09687 | 0.03951 | 0.0188 |
| CA-145 | 0.003156 | 0.002046 | | | | 0.003646 | 0.00601 | 0.00267 | 0.008117 |
| CA-149 | 6.692 | | 1.228 | 4.657 | ~18.74 | 2.211 | 10.02 | 2.599 | 3.648 |
| CA-155 | 0.2656 | 0.743 | | 0.2926 | 0.1839 | 0.1899 | 0.6945 | 0.3736 | 0.2049 |
| CA-157 | 0.008283 | 0.01041 | 0.001367 | 0.008761 | 0.5651 | 0.7224 | 0.08469 | 0.003114 | 0.007651 |
| CA-158 | 2.209 | 10.36 | ~17.76 | ~36.89 | 3.81 | 2.623 | | 2.07 | 1.524 |
| CA-159 | 0.007067 | 0.003842 | | 0.003769 | 0.001155 | 0.001525 | 0.00663 | 0.001758 | |
| CA-162 | 0.05936 | 0.03304 | 0.003047 | 0.02429 | 0.06352 | 0.02211 | 0.3922 | 0.006071 | 0.007555 |
| CA-165-2 | 7.516 | 10.6 | 0.2398 | 3.767 | ~30.67 | | 12.1 | ~38.45 | 0.9827 |
| CA-167 | 0.02315 | 0.01101 | 0.00669 | 0.003628 | 0.008135 | 0.006256 | 0.04668 | 0.003155 | 0.00794 |
| CA-170 | 0.07188 | 0.2972 | 0.9829 | 0.06628 | 0.05196 | 0.03358 | 0.3786 | 0.02508 | 0.03578 |
| CA-171 | 0.00729 | 0.01128 | | 0.003488 | 0.003794 | 0.007502 | 0.09852 | 0.00155 | 0.006213 |
| CA-173 | 0.01565 | 0.007537 | 0.005323 | 0.002746 | 0.01857 | 0.01019 | 0.04347 | 0.005288 | 0.02111 |
| CA-179 | 0.006802 | 0.007599 | 0.002671 | 0.007227 | 0.007953 | 0.002721 | 0.0479 | 0.004389 | 0.01774 |
| CA-178 | 0.1581 | 0.1507 | 0.2499 | 0.8769 | 0.4669 | 0.5306 | 0.4599 | 0.2555 | 0.1409 |
| CA-182 | 0.003007 | 0.003813 | | 0.002021 | 0.001855 | 0.004691 | 0.02065 | 0.004115 | 0.009074 |
| CA-183 | 0.0007893 | | 1.536E-14 | | | 0.001349 | 0.0008805 | 0.001326 | 0.0007859 |
| CA-184 | 0.02938 | 0.2235 | 0.06488 | 0.2251 | 0.6153 | 0.2113 | 0.3446 | 0.02228 | 0.3106 |
| CA-187 | 0.04405 | 0.02811 | 0.01676 | 0.06414 | 0.08156 | 0.03139 | 0.2035 | 0.01967 | 0.00897 |
| CA-190 | 0.01399 | 0.003469 | 0.005293 | | 0.004934 | 0.003265 | 0.01138 | 0.007009 | 0.003565 |
| CA-193 | 0.02785 | 0.02444 | 0.03952 | 0.05131 | 0.03841 | 0.02375 | 0.108 | 0.01697 | 0.01137 |
| CA-194 | 0.004494 | 0.005049 | 0.004454 | | 0.003434 | 0.0009551 | 0.04819 | 0.003275 | 0.003139 |
| ca-196 | 0.003626 | 0.003735 | 0.001711 | | 0.001518 | 0.003008 | 0.009935 | 0.002681 | 0.002753 |
| ca-197 | 3.738 | 10.3 | 0.04547 | 2.974 | 0.2369 | 0.3767 | 1.244 | 0.4882 | 0.00915 |
| CA-202 | 0.007805 | 0.009448 | 0.00203 | | 0.002734 | 0.004999 | 0.01796 | 0.001773 | 0.008545 |
| CA-203 | 0.01374 | 0.04586 | 0.05916 | 0.05046 | 0.05406 | 0.0379 | 0.1913 | 0.04516 | 0.122 |
| CA-207 | 0.01696 | 0.006162 | 0.002354 | | 0.00287 | 0.005695 | 0.01562 | 0.006109 | 0.003519 |
| CA-211 | 0.00937 | 0.003681 | 0.002339 | | 0.004395 | 0.02289 | 0.02043 | 0.003595 | 0.02341 |
| CA-218 | 0.01283 | 0.03272 | 0.1527 | 0.01038 | 0.0278 | 0.004522 | 0.1279 | 0.008768 | 0.01432 |
| CA-219 | 0.06668 | 0.2317 | 1.187 | 0.03732 | 0.08025 | 0.0558 | 0.6559 | 0.01159 | 0.03984 |
| EL-1004 | 0.01811 | 0.06444 | 0.4042 | 0.03859 | 0.02319 | 0.007455 | 0.1284 | 0.01783 | 0.01697 |
| EL-1007 | 0.02462 | 0.03473 | 0.02991 | 0.007199 | 0.03236 | 0.008386 | 0.06154 | 0.01687 | 0.01199 |
| EL-1012 | 0.008054 | 0.005124 | 0.01378 | 0.002949 | 0.002288 | | 0.0172 | 0.005312 | 0.006108 |
| EL-1050 | 0.002862 | 0.001657 | | | | 0.0005105 | 0.001525 | | 0.001472 |
| EL-1051 | 0.004569 | 0.003025 | 0.0006296 | | 0.005603 | 0.001691 | 0.003057 | 0.00156 | 0.002912 |
| EL-1059 | 0.00648 | 0.002126 | 0.0008934 | 0.002376 | 0.004731 | 0.002106 | 0.00654 | 0.002315 | 0.006168 |
| EL-1062 | 0.005063 | 0.006301 | 0.006191 | | 0.0014 | 0.001556 | 0.0266 | 0.003068 | 0.007918 |

TABLE 4-continued

Rate constants for each ligand with each mutant Cdk2

| | Protein | | | | | | | | |
|---|---|---|---|---|---|---|---|---|---|
| | Glutathione | Cdk2 | Cdk2 | Cdk2 | Cdk2 | Cdk2 | Cdk2 | Cdk2 | Cdk2 |
| | | | | | Cysteine position | | | | |
| | NA | WT | F80C | H71C | S276C | N272C | T182C | R122C | S181C |
| Ligand name | — | | C177A | C177A | C177A | C177A | C177A | C177A | C177A |
| | | | | | Additional mutations | | | | |
| EL-1063 | 0.003394 | 0.002743 | 0.009353 | 0.003705 | 0.001905 | 0.003977 | 0.03082 | 0.002484 | 0.005297 |
| EL-1064 | 0.01195 | 0.00589 | 0.01966 | 0.01034 | 0.01284 | 0.01262 | 0.02031 | 0.006914 | 0.01756 |
| EL-1071 | 0.05081 | 0.433 | 3.073 | 0.3666 | 0.05538 | 0.03091 | 0.3945 | 0.01447 | 0.02559 |
| EL-1074 | 0.01025 | 0.006082 | 0.004669 | 0.002542 | 0.004381 | 0.006635 | 0.01875 | 0.0033 | 0.002194 |
| EL-1083 | 0.01092 | 0.0009768 | | | 0.005508 | 0.001714 | 0.00998 | 0.0005988 | 0.001672 |
| EL-1084 | 0.004273 | 0.005012 | 7.515E-14 | | 0.001759 | 0.002598 | 0.007812 | 0.0009787 | 0.0003879 |
| EL-1098 | 0.01151 | 0.01063 | 0.008291 | 0.002978 | 0.0117 | 0.009773 | 0.02907 | 0.006443 | 0.00499 |
| EL-1101 | 0.007427 | 0.003421 | 0.002538 | 0.006227 | 0.007413 | 0.005051 | 0.009691 | 0.002286 | 0.002941 |
| EL-1109 | 0.008572 | 0.008316 | 0.01663 | 0.004838 | 0.007876 | 0.003319 | 0.04531 | 0.006219 | 0.01361 |
| EL-1114 | 0.03014 | 0.07947 | 0.2784 | 0.1021 | 0.02403 | 0.001386 | 0.4929 | 0.007805 | 0.01188 |
| EL-1121 | 0.02567 | 0.01328 | 0.01257 | 0.03901 | 0.0198 | 0.01425 | 0.03623 | 0.006872 | 0.02699 |
| EL-1140 | 0.008126 | 0.00499 | 0.005854 | | 0.001645 | 0.0009109 | 0.01087 | 0.003006 | 0.005455 |
| EL-1134 | 0.004413 | 0.007099 | 0.01742 | 0.02042 | 0.006242 | 0.004938 | 0.06354 | 0.005054 | 0.007065 |
| EL-1143 | 0.008837 | 0.03792 | 0.009355 | 0.002426 | 0.03045 | 0.01321 | 0.1517 | 0.002778 | 0.021 |
| EL-1152 | 0.005936 | 0.007039 | 0.004844 | 0.003943 | 0.01203 | 0.001935 | 0.02276 | 0.004438 | 0.005678 |
| EL-1153 | 0.002823 | 0.001028 | | | 7.68E-14 | 0.0128 | 0.001338 | 0.00274 | 0.002097 |
| EL-1155 | 0.01124 | 0.004658 | 0.003532 | 0.00523 | 0.01513 | 0.01235 | 0.02393 | 0.006445 | 0.006043 |
| EL-1156 | 0.01759 | 0.01873 | 0.01786 | 0.006834 | 0.02375 | 0.005976 | 0.07206 | 0.0121 | 0.01759 |
| EL-1157 | 0.06726333 | 0.2006 | 0.03933 | 0.02618 | 0.07038 | 0.002862 | 0.1572 | 0.004819 | 0.01381 |
| EL-1160 | 0.02865 | 0.01181 | 0.01348 | 0.02783 | 0.02201 | 0.0163 | 0.05729 | 0.007767 | 0.01342 |
| EL-1164 | 0.007698 | 0.003662 | 0.002151 | | 2.302E-14 | 0.0007233 | 0.001408 | | 0.007559 |
| EL-1168 | 0.01334 | 0.009736 | 0.004166 | 0.01145 | 0.008034 | 0.008745 | 0.03904 | 0.004032 | 0.02323 |
| EL-1170 | 0.002427 | 0.004821 | 0.001226 | | 0.0007587 | 0.0008836 | 0.001391 | 0.0007379 | 0.002313 |
| EL-1178 | 0.04821 | 0.1611 | 0.09345 | 0.02706 | 0.04503 | 0.008888 | 0.2419 | 0.02367 | 0.02566 |
| EL-1176 | 0.0009643 | 0.0006931 | 0.002745 | 0.001174 | 0.00199 | 0.002431 | | | 0.0006332 |
| EL-1183 | 0.006554 | 0.003762 | 0.01874 | 0.01195 | 0.005301 | 0.002748 | 0.01481 | 0.003828 | 0.005591 |
| EL-1187 | 0.01328 | 0.00921 | 0.005875 | 0.005929 | 0.005321 | 0.00704 | 0.05839 | 0.001907 | 0.003834 |
| EL-1174 | 0.004201 | 0.001449 | 0.01365 | 0.003601 | 0.003008 | | 0.005783 | 0.002235 | 0.002125 |
| CA-236 | 0.009189 | 0.001156 | 0.003744 | 0.001749 | 0.0006497 | 0.0009059 | 0.009576 | 0.001846 | 0.002114 |
| BN-62 | 0.001539 | 0.002863 | 0.001062 | 3.908E-14 | 0.001184 | 0.001549 | 0.001045 | 0.0001923 | 1.74E-14 |
| BN-346 | 0.004652 | 0.005514 | 0.0008792 | 0.0004445 | 0.0009323 | 0.001994 | 0.000862 | | 0.001084 |
| BN-80 | 0.02983 | 0.0419 | 0.03902 | 0.003721 | 0.01797 | 0.006181 | 0.1201 | 0.01649 | 0.0138 |
| GC248 | 0.01493 | 0.01361 | 0.001799 | 0.009473 | 0.002781 | 0.01579 | 0.5214 | 0.01243 | 0.01548 |
| CA-53 | 0.004301 | 0.000968 | 0.009547 | 0.005009 | 0.004301 | 0.006086 | 0.05877 | 0.004377 | 0.06402 |
| CA-106 | 0.003956 | 0.002317 | | | 0.002984 | 0.01199 | 0.01571 | 0.001115 | 0.006686 |
| CA-118 | 0.006004 | 0.0105 | 0.003604 | 0.001184 | 0.002454 | 0.3682 | | 0.001844 | 0.02877 |
| CA-152 | 8.003 | 3.498 | 1.27 | | | | | | 7.297 |
| CA-165-1 | 5.198 | 5.676 | 3.436 | | | | | | |
| CA-188 | 0.1987 | 0.55 | 0.5106 | 0.3055 | 0.007587 | 0.06304 | 0.3741 | 0.01775 | 0.04931 |
| CA-192 | 0.01342 | 0.00584 | 0.001553 | 0.002926 | 0.001086 | 0.004987 | 0.006134 | 0.001825 | 0.00198 |
| CA216 | 0.004286 | 0.01619 | 0.07999 | 0.004427 | 0.007064 | 0.01252 | 0.2557 | 0.001824 | 0.003795 |
| CA-224 | 0.003765 | 0.001548 | 0.000611 | 0.003169 | 0.0006465 | 0.002107 | 0.004866 | | |
| BN-63 | 0.002052 | 0.002998 | 0.001168 | 6.534E-14 | 0.0008064 | 0.001026 | 0.001476 | | 0.0009 |
| BN-65 | 0.002366 | 0.001861 | 0.006255 | 0.001273 | 0.002789 | 0.002156 | 0.002061 | | 0.001226 |
| BN-66 | 0.001496 | 0.001459 | 0.003494 | 0.00113 | | 0.002323 | 0.005204 | | 0.001268 |
| BN-78 | 0.007274 | 0.001157 | 0.001773 | | 0.00118 | 0.003673 | 0.0009576 | 0.00174 | 0.0006548 |
| BN122 | 0.005992 | 0.002191 | 0.002336 | | 0.0009842 | 0.004448 | 0.01499 | 0.002587 | 0.005838 |
| EN001 | 6.115 | 9.832 | 0.00407 | 2.131 | 3.146 | 2.432 | 8.524 | 1.352 | 0.4008 |
| EN002 | | 0.006451 | 0.2493 | 3.825E-14 | | 0.00573 | 0.01298 | 0.0006932 | 0.001495 |
| EN003 | | 0.003627 | 0.01484 | | 0.004134 | 0.002228 | 0.003946 | 0.0005805 | 0.002251 |
| EN004 | 0.366 | 1.596 | 0.006096 | 0.1289 | 1.689 | 0.08895 | | 0.04566 | 0.03286 |
| EN005 | 0.002533 | 0.01562 | 0.002202 | 0.002158 | 0.03433 | | 0.02869 | 0.001439 | 0.01491 |
| EN006 | 0.002219 | 0.002918 | 1.724E-14 | 0.02873 | 0.1659 | 0.01282 | 0.07618 | 0.000912 | 0.01045 |
| EN007 | | | 0.001332 | | | 0.001652 | 0.001386 | | |
| EN008 | | | 0.2076 | | 6.908E-15 | 0.009116 | 0.005911 | | 0.001089 |
| EN009 | | | 0.02092 | 3.52E-14 | 0.005935 | | 0.006898 | 0.0008504 | 0.004061 |
| EN010 | 0.603 | 1.708 | 0.005192 | 0.06183 | 0.5747 | 0.1194 | 2.544 | 0.2291 | 0.1896 |
| EN011 | 0.1325 | 0.08018 | | 0.0114 | 0.1424 | 0.01938 | 0.06061 | 0.002863 | 0.01298 |
| EN012 | 0.27 | 0.2933 | | 0.009738 | 0.1594 | 0.02849 | 0.08536 | 0.00759 | 0.01809 |

TABLE 5

Rate enhancements for each ligand with each mutant Cdk2

| Ligand | Cdk2 WT | Cdk2 F80C C177A | Cdk2 H71C C177A | Cdk2 S276C C177A | Cdk2 N272 C177A | Cdk2 T182C C177A | Cdk2 R122C C177A | Cdk2 S181C C177A |
|---|---|---|---|---|---|---|---|---|
| CA-009 | 2.40372226 | 0.50293486 | 0.28360773 | 0.81861131 | 1.31796707 | 21.5748031 | 0.5793844 | 0.47072298 |
| CA-012 | 1.85466795 | 3.88835419 | 0.31703561 | 0.98517806 | 0.41886429 | 5.79980751 | 0.68970164 | 2.50433109 |
| CA-028 | 2.83494193 | 1.17536398 | 1.03500736 | 1.03975135 | 0.76116473 | 5.24619663 | 0.34745624 | 0.50662522 |
| CA-029 | 0.42260664 | 0.1235545 | 0.12663507 | 0.32720379 | 0.27194313 | 1.76587678 | 0.20327014 | 0.32981043 |
| CA-030 | 0.63897191 | 1.49432158 | 0.13173939 | 0.26569038 | 0.24088464 | 0.59569635 | 0.28959952 | 0.74775852 |
| CA-031 | 0.17655172 | 0.02876437 | 0 | 0.52942529 | 1.16896552 | 1.06264368 | 0.22103448 | 0.56143678 |
| CA-032/228 | 1.40525672 | 2.23166259 | 15.3606357 | 1.85146699 | 3.00672372 | 14.804401 | 1.53361858 | 1.04339853 |
| CA-034 | 1.0525176 | 1.27828912 | 1.74986465 | 2.71792095 | 0.7222523 | 10.146183 | 0.64158094 | 0.58581483 |
| CA-037 | 3.30804749 | 63.5883905 | 1.96372032 | 1.76319261 | 1.73878628 | 12.3021108 | 0.96965699 | 1.49538259 |
| CA-038 | 0.52175066 | 0 | 0.82537577 | 0.58275862 | 0.59204244 | 1.74447392 | 0.36914235 | 0.47152962 |
| CA-039 | 0.28019656 | 0 | 0 | 1.13955774 | 0.74987715 | 1.42506143 | 0.88894349 | 0.63341523 |
| CA-040/230 | 0.69146455 | 0.31016791 | 0.73344216 | 0.76539179 | 3.07602612 | 1.26772388 | 0.28498134 | 0.24696828 |
| CA-041 | 2.08136578 | 0 | 0.00720668 | 0.00640029 | 0.00858928 | 0.85543044 | 0.00395568 | 0.00575554 |
| CA-042 | 2.90977444 | 0.42870813 | 0.50642515 | 0.56356801 | 0.09535202 | 5.5468216 | 0.1215311 | 0.31872864 |
| CA-044 | 0.33071446 | 0 | 0 | 0.11155168 | 0 | 0.29032654 | 0.23017432 | 0.11341763 |
| CA-046 | 0.21042305 | 0.11630901 | 0.07112201 | 0.70692826 | 0.09294911 | 0.59503372 | 0.23973023 | 0.19865113 |
| CA-047 | 0.45528455 | 0.13065041 | 0 | 0.54642276 | 0.16650407 | 1.06341463 | 0.26284553 | 0.27658537 |
| CA-048 | 0.7117927 | 0.80222105 | 0.23310418 | 0.77895293 | 0.54415653 | 2.64463247 | 0.20232681 | 0.60285563 |
| CA-054 | 0.61627369 | 1.48196949 | 1.02311604 | 0.94983819 | 1.24757282 | 1.05917707 | 0.41978733 | 0.46971798 |
| CA-055 | 0.40659387 | 0 | 0.48593028 | 0.69718606 | 4.59050819 | 0.26211676 | 0.42881142 | 1.07349853 |
| CA-056 | 1.15040184 | 4.98392652 | 1.2543054 | 1.7761194 | 1.54764638 | 18.3524684 | 0.78185993 | 2.06888634 |
| CA-057 | 2.7008676 | 2.13919276 | 1.63636364 | 1.60618634 | 2.88532629 | 18.5137684 | 1.17615994 | 1.06903055 |
| CA-060 | 0.71428571 |  | 0 | 1.11152199 | 3.67652783 | 1.61930712 | 0.46749708 | 0.78123784 |
| CA-072 | 1.0850968 | 0.25664115 | 16.4565511 | 4.03647006 | 9.38766321 | 6.71769473 | 0.35029266 | 2.16704187 |
| CA-079 | 1.01810691 | 0.14084354 | 0.29979399 | 0.66485959 | 0.49159709 | 0.83660414 | 0.4828147 | 4.96042502 |
| CA-080/239 | 0.23172757 | 0.08363787 | 0 | 0.28853821 | 0.2755814 | 0.96511628 | 0.17300664 | 0.13770764 |
| CA-081/240 | 7.59948652 | 4.62130937 | 0.90415062 | 7.41121095 | 3.27642276 | 8.31407788 | 0.70988447 | 9.93581515 |
| CA-084 | 0.51861987 | 1.81082689 | 0.82093992 | 1.07852469 | 0.06817371 | 3.84830458 | 0.26936347 | 0.42581797 |
| CA-087 | 1.05910165 | 0.478487 | 35.5319149 | 0.7321513 | 0.30449173 | 6.46453902 | 0.31903073 | 0.64574468 |
| CA-088 | 0.30544427 | 0.12054443 | 0 | 0.43949666 | 0.56086287 | 0.90960452 | 0.46836158 | 0.19044684 |
| CA-089 | 4.33596248 | 1.90854828 | 3.47473886 | 3.06118098 | 4.34448945 | 16.7128544 | 0.46216159 | 0.57535707 |
| CA-091/238 | 0.29683667 | 0.10282763 | 0.19444803 | 0.93957392 | 0.37688832 | 2.00258231 | 0.69180116 | 1.13892834 |
| CA-092 | 3.15222595 | 0.10581618 | 2.68908569 | 6.52824318 | 7.16251795 | 6.48276687 | 2.26902824 | 0.91455242 |
| CA-093 | 0.25731523 | 1.27149321 | 0.57526395 | 1.32730015 | 0.42066553 | 4.07164404 | 0.31101056 | 0.7760181 |
| CA-096/146 | 0.30231111 | 1.64088889 | 0.88888889 | 1.27644444 | 0.89066667 | 10.32 | 0.71422222 | 12.9688889 |
| CA-097 | 0.1544013 | 0.18865623 | 0.15663753 | 0.81408823 | 0.58975402 | 1.44744867 | 0.34986786 | 0 |
| CA-098 | 0.94457455 | 0.59289617 | 0.80015613 | 3.19594067 | 6.69789227 | 4.76580796 | 0.34808743 | 0.8871975 |
| CA-099/153 | 1.36552049 | 0.16514366 | 0.29072068 | 2.2656618 | 2.39331135 | 2.03768252 | 2.42345737 | 1.4790391 |
| CA-129/235 | 0.25077768 | 0.18188472 | 0.03270814 | 1.68161025 | 0.39359561 | 0.88261665 | 0.92497713 | 0.22268984 |
| CA-141 | 0.38473918 | 0.09517203 | 0 | 0 | 0.25066593 | 0.51248613 | 0.23862375 | 0.19350721 |
| CA-142 | 1.52169625 | 9.63510848 | 0.17968442 | 3.67998028 | 0.3071499 | 12.8648915 | 0.13185404 | 0.40285996 |
| CA-143 | 0.38028649 | 0.10136426 | 0.08025239 | 0.63437926 | 0.49420191 | 2.35914052 | 0.20494543 | 0.91780355 |
| CA-144 | 1.12466971 | 0.49555609 | 8.25606534 | 1.2615902 | 2.14004324 | 2.3269277 | 0.94907519 | 0.45159741 |
| CA-145 | 0.64828897 | 0 | 0 | 0 | 1.15525982 | 1.90430925 | 0.8460076 | 2.57192649 |
| CA-149 | 0 | 0.18350269 | 0.69590556 | 0 | 0.3303945 | 1.49731022 | 0.38837418 | 0.54512851 |
| CA-155 | 2.79743976 | 0 | 1.10165663 | 0.69239458 | 0.71498494 | 2.61483434 | 1.40662651 | 0.77146084 |
| CA-157 | 1.25679102 | 0.16503682 | 1.05770856 | 68.2240734 | 87.2147773 | 10.2245563 | 0.37595074 | 0.92369914 |
| CA-158 | 4.68990493 |  | 0 | 1.72476234 | 1.18741512 | 0 | 0.9370756 | 0.68990493 |
| CA-159 | 0.5436536 | 0 | 0.5333239 | 0.16343569 | 0.21579171 | 0.93816329 | 0.24876185 | 0 |
| CA-162 | 0.55660377 | 0.05133086 | 0.40919811 | 1.07008086 | 0.37247305 | 6.60714286 | 0.10227426 | 0.12727426 |
| CA-165-2 | 1.41032464 | 0.03190527 | 0.50119745 | 0 | 0 | 1.60989888 |  | 0.13074774 |
| CA-167 | 0.47559395 | 0.28898488 | 0.15671706 | 0.35140389 | 0.27023758 | 2.01641469 | 0.1362851 | 0.34298056 |
| CA-170 | 4.13466889 | 13.6741792 | 0.92209238 | 0.72287145 | 0.4671675 | 5.26711185 | 0.34891486 | 0.49777407 |
| CA-171 | 1.5473251 | 0 | 0.47846365 | 0.52043896 | 1.02908093 | 13.5144033 | 0.21262003 | 0.85226337 |
| CA-173 | 0.48159744 | 0.3401278 | 0.17546326 | 1.18658147 | 0.65111821 | 2.77763578 | 0.33789137 | 1.34888179 |
| CA-179 | 1.11717142 | 0.39267862 | 1.06248162 | 1.16921494 | 0.4000294 | 7.04204646 | 0.6452514 | 2.60805645 |
| CA-178 | 0.95319418 | 1.58064516 | 5.54648956 | 2.95319418 | 3.35610373 | 2.90891841 | 1.61606578 | 0.8912081 |
| CA-182 | 1.26804124 | 0 | 0.67209844 | 0.61689391 | 1.5600266 | 6.86730961 | 1.36847356 | 3.01762554 |
| CA-183 | 0 | 1.946E-11 | 0 | 0 | 1.70910934 | 1.11554542 | 1.67996959 | 0.99569239 |
| CA-184 | 7.60721579 | 2.20830497 | 7.66167461 | 20.9428182 | 7.19196732 | 11.7290674 | 0.75833901 | 10.5718176 |
| CA-187 | 0.63813848 | 0.38047673 | 1.45607264 | 1.85153235 | 0.71259932 | 4.61975028 | 0.44653802 | 0.20363224 |
| CA-190 | 0.24796283 | 0.37834167 | 0 | 0.35268049 | 0.23338099 | 0.81343817 | 0.50100071 | 0.25482487 |
| CA-193 | 0.87755835 | 1.41903052 | 1.84236984 | 1.37917415 | 0.85278276 | 3.87791741 | 0.60933573 | 0.40825853 |
| CA-194 | 1.123498 | 0.99109924 | 0 | 0.76412995 | 0.21252781 | 10.7231865 | 0.72874944 | 0.69848687 |
| ca-196 | 1.03006067 | 0.47186983 | 0 | 0.41864313 | 0.82956426 | 2.73993381 | 0.73938224 | 0.75923883 |
| ca-197 | 2.75548422 | 0.01216426 | 0.79561263 | 0.06337614 | 0.10077582 | 0.33279829 | 0.1306046 | 0.00244783 |
| CA-202 | 1.21050609 | 0.26008969 | 0 | 0.35028828 | 0.64046087 | 2.30108905 | 0.22716208 | 1.09481102 |
| CA-203 | 3.33770015 | 4.30567686 | 3.67248908 | 3.93449782 | 2.75836972 | 13.922853 | 3.286754 | 8.87918486 |
| CA-207 | 0.36332547 | 0.13879717 | 0 | 0.1692217 | 0.33579009 | 0.92099057 | 0.36020047 | 0.20748821 |
| CA-211 | 0.39284952 | 0.24962647 | 0 | 0.46905016 | 2.44290288 | 2.18036286 | 0.38367129 | 2.49839915 |
| CA-218 | 2.5502728 | 11.9017927 | 0.80904131 | 2.16679657 | 0.35245518 | 9.96882307 | 0.68339829 | 1.11613406 |
| CA-219 | 3.47480504 | 17.8014397 | 0.55968806 | 1.2035093 | 0.83683263 | 9.83653269 | 0.17381524 | 0.5974805 |

TABLE 5-continued

Rate enhancements for each ligand with each mutant Cdk2

| | Cdk2 WT | Cdk2 F80C | Cdk2 H71C | Cdk2 S276C | Cdk2 N272 | Cdk2 T182C | Cdk2 R122C | Cdk2 S181C |
|---|---|---|---|---|---|---|---|---|
| | | | | | Additional mutations | | | |
| Ligand | — | C177A | C177A | C177A | C177A | C177A | C177A | C177A |
| EL-1004 | 3.55825511 | 22.3191607 | 2.13086692 | 1.28050801 | 0.41165102 | 7.09000552 | 0.98453893 | 0.93705135 |
| EL-1007 | 1.41064175 | 1.21486596 | 0.29240455 | 1.31437855 | 0.34061738 | 2.49959383 | 0.68521527 | 0.48700244 |
| EL-1012 | 0.63620561 | 1.71095108 | 0.36615346 | 0.28408244 | 0 | 2.1355848 | 0.65954805 | 0.75838093 |
| EL-1050 | 0.57896576 | 0 | 0 | 0 | 0.17837177 | 0.53284416 | 0 | 0.51432565 |
| EL-1051 | 0.66207047 | 0.13779821 | 0 | 1.22630773 | 0.37010287 | 0.6690742 | 0.34143139 | 0.63733859 |
| EL-1059 | 0.32808642 | 0.13787037 | 0.36666667 | 0.73009259 | 0.325 | 1.00925926 | 0.35725309 | 0.95185185 |
| EL-1062 | 1.24451906 | 1.22279281 | 0 | 0.2765159 | 0.30732767 | 5.25380209 | 0.60596484 | 1.56389492 |
| EL-1063 | 0.80819093 | 2.75574543 | 1.09163229 | 0.56128462 | 1.17177372 | 9.0807307 | 0.73187979 | 1.56069534 |
| EL-1064 | 0.49288703 | 1.64518828 | 0.86527197 | 1.07447699 | 1.05606695 | 1.69958159 | 0.57857741 | 1.46945607 |
| EL-1071 | 8.5219445 | 60.4802204 | 7.21511513 | 1.08994292 | 0.60834481 | 7.76421964 | 0.28478646 | 0.50364102 |
| EL-1074 | 0.59336585 | 0.4555122 | 0.248 | 0.42741463 | 0.64731707 | 1.82926829 | 0.32195122 | 0.21404878 |
| EL-1083 | 0.08945055 | 0 | 0 | 0.5043956 | 0.15695971 | 0.91391941 | 0.05483516 | 0.15311355 |
| EL-1084 | 1.17294641 | 1.7587E−11 | 0 | 0.41165458 | 0.60800374 | 1.82822373 | 0.22904283 | 0.09077931 |
| EL-1098 | 0.92354474 | 0.72033015 | 0.25873154 | 1.01650738 | 0.84908775 | 2.52562989 | 0.55977411 | 0.43353606 |
| EL-1101 | 0.46061667 | 0.34172613 | 0.83842736 | 0.99811499 | 0.68008617 | 1.30483371 | 0.30779588 | 0.39598761 |
| EL-1109 | 0.97013532 | 1.94003733 | 0.56439571 | 0.91880541 | 0.38719085 | 5.28581428 | 0.72550163 | 1.58772748 |
| EL-1114 | 2.63669542 | 9.23689449 | 3.38752488 | 0.79727936 | 0.0459854 | 16.3536828 | 0.2589582 | 0.39416058 |
| EL-1121 | 0.51733541 | 0.48967667 | 1.51967277 | 0.7713284 | 0.55512271 | 1.41137515 | 0.26770549 | 1.05142189 |
| EL-1140 | 0.61407827 | 0.72040364 | 0 | 0.20243662 | 0.11209697 | 1.33768152 | 0.3699237 | 0.67130199 |
| EL-1134 | 1.60865624 | 3.94742805 | 4.62723771 | 1.41445729 | 1.11896669 | 14.3983685 | 1.14525266 | 1.60095173 |
| EL-1143 | 4.291049 | 1.05861718 | 0.27452755 | 3.4457395 | 1.49485119 | 17.1664592 | 0.31436008 | 2.37637207 |
| EL-1152 | 1.18581536 | 0.81603774 | 0.66425202 | 2.02661725 | 0.32597709 | 3.83423181 | 0.74764151 | 0.95653639 |
| EL-1153 | 0.36415161 | 0 | 0 | 2.7205E−11 | 4.53418349 | 0.47396387 | 0.97059865 | 0.74282678 |
| EL-1155 | 0.41441281 | 0.31423488 | 0.46530249 | 1.34608541 | 1.0985445 | 2.12900356 | 0.57339858 | 0.53763345 |
| EL-1156 | 1.06480955 | 1.01534963 | 0.3885162 | 1.35019898 | 0.33973849 | 4.09664582 | 0.68789085 | 1 |
| EL-1157 | 2.98230834 | 0.58471678 | 0.38921651 | 1.0463353 | 0.04254918 | 2.33708311 | 0.07164379 | 0.20531245 |
| EL-1160 | 0.4122164 | 0.47050611 | 0.97137871 | 0.76823735 | 0.56893543 | 1.99965096 | 0.27109948 | 0.46841187 |
| EL-1164 | 0.47570798 | 0.27942323 | 0 | 2.9904E−12 | 0.09395947 | 0.18290465 | 0 | 0.98194336 |
| EL-1168 | 0.72983508 | 0.31229385 | 0.85832084 | 0.60224888 | 0.65554723 | 2.92653673 | 0.30224888 | 1.74137931 |
| EL-1170 | 1.98640297 | 0.50515039 | 0 | 0.31260816 | 0.36407087 | 0.57313556 | 0.30403791 | 0.95302843 |
| EL-1178 | 3.34163037 | 1.93839452 | 0.56129434 | 0.93403858 | 0.18436009 | 5.0176312 | 0.49097698 | 0.53225472 |
| EL-1176 | 0.71875972 | 2.84662449 | 1.21746344 | 2.06367313 | 2.52099969 | 0 | 0 | 0.65664212 |
| EL-1183 | 0.57400061 | 2.85932255 | 1.82331401 | 0.80881904 | 0.41928593 | 2.25968874 | 0.5840708 | 0.85306683 |
| EL-1187 | 0.6935241 | 0.44239458 | 0.44646084 | 0.40067771 | 0.53012048 | 4.39683735 | 0.1435994 | 0.28870482 |
| EL-1174 | 0.34491788 | 3.24922637 | 0.85717686 | 0.71602 | 0 | 1.37657701 | 0.53201619 | 0.50583194 |
| CA-236 | 0.12580259 | 0.40744368 | 0.19033627 | 0.0707041 | 0.09858526 | 1.04211557 | 0.20089237 | 0.23005768 |
| BN-62 | 1.8602989 | 0.69005848 | 2.5393E−11 | 0.76933073 | 1.00649773 | 0.67901235 | 0.12495127 | 1.1306E−11 |
| BN-346 | 1.18529665 | 0.18899398 | 0.0955503 | 0.20040843 | 0.42863285 | 0.18529665 | 0 | 0.23301806 |
| BN-80 | 1.40462622 | 1.30807911 | 0.12474019 | 0.60241368 | 0.20720751 | 4.02614817 | 0.5527992 | 0.46262152 |
| GC248 | 0.91158741 | 0.12049565 | 0.63449431 | 0.18626926 | 1.05760214 | 34.9229739 | 0.83255191 | 1.03683858 |
| CA-53 | 0.22506394 | 2.21971635 | 1.16461288 | 1 | 1.41501976 | 13.6642641 | 1.01767031 | 14.8849105 |
| CA-106 | 0.58569262 | 0 | 0 | 0.75429727 | 3.03083923 | 3.97118301 | 0.28185035 | 1.690091 |
| CA-118 | 1.74883411 | 0.60026649 | 0.19720187 | 0.40872751 | 61.3257828 | 0 | 0.30712858 | 4.79180546 |
| CA-152 | 0.43708609 | 0.15869049 | 0 | 0 | 0 | 0 | 0 | 0.91178308 |
| CA-165-1 | 1.09195845 | 0.66102347 | 0 | 0 | 0 | 0 | 0 | 0 |
| CA-188 | 2.76799195 | 2.56970307 | 1.53749371 | 0.03818319 | 0.3172622 | 1.8827378 | 0.08933065 | 0.24816306 |
| CA-192 | 0.43517139 | 0.1157228 | 0.21803279 | 0.08092399 | 0.37160954 | 0.45707899 | 0.13599106 | 0.14754098 |
| CA216 | 3.77741484 | 18.6630891 | 1.03289781 | 1.64815679 | 2.92113859 | 59.659356 | 0.42557163 | 0.88544097 |
| CA-224 | 0.41115538 | 0.1622842 | 0.84169987 | 0.17171315 | 0.55962815 | 1.29243028 | 0 | 0 |
| BN-63 | 1.46101365 | 0.56920078 | 3.1842E−11 | 0.39298246 | 0.5 | 0.71929825 | 0 | 0.43859649 |
| BN-65 | 0.78655959 | 2.64370245 | 0.53803888 | 1.17878276 | 0.9112426 | 0.87109045 | 0 | 0.51817413 |
| BN-66 | 0.97526738 | 2.3355615 | 0.75534759 | 0 | 1.55280749 | 3.47860963 | 0 | 0.84759358 |
| BN-78 | 0.15905966 | 0.24374484 | 0 | 0.16222161 | 0.50494913 | 0.13164696 | 0.23920814 | 0.09001925 |
| BN122 | 0.36565421 | 0.38985314 | 0 | 0.16425234 | 0.7423231 | 2.50166889 | 0.43174232 | 0.97429907 |
| EN001 | 1.60784955 | 0.00066558 | 0.34848733 | 0.51447261 | 0.39771055 | 1.3939493 | 0.22109567 | 0.06554374 |
| EN002 | 1.27589299 | 49.307103 | 7.5652E−12 | 0 | 1.13329202 | 2.56721299 | 0.13710262 | 0.29568439 |
| EN003 | 0.77778373 | 3.18232992 | 0 | 0.88650619 | 0.47777837 | 0.84619096 | 0.124484 | 0.48271056 |
| EN004 | 4.36065574 | 0.01665574 | 0.35218579 | 4.6147541 | 0.24303279 | 0 | 0.1247541 | 0.08978142 |
| EN005 | 6.16660087 | 0.86932491 | 0.8519542 | 13.5530991 | 0 | 11.3264903 | 0.56810107 | 5.88630083 |
| EN006 | 1.31500676 | 7.7693E−12 | 12.9472735 | 74.7634069 | 5.7773772 | 34.3307796 | 0.41099594 | 4.70932853 |
| EN007 | 0 | 0.91441648 | 0 | 0 | 0 | 0.95148741 | | |
| EN008 | 0 | 4.63981119 | 0 | 1.5439E−13 | 0.20374046 | 0.13210946 | 0 | 0.02433889 |
| EN009 | 0 | 3.2463972 | 5.4624E−12 | 0.92100227 | 0 | 1.07044206 | 0.13196636 | 0.63019211 |
| EN010 | 2.83250415 | 0.00861028 | 0.10253731 | 0.95306799 | 0.19800995 | 4.21890547 | 0.37993367 | 0.31442786 |
| EN011 | 0.60513208 | 0 | 0.08603774 | 1.07471698 | 0.14626415 | 0.45743396 | 0.02160755 | 0.09796226 |
| EN012 | 1.0862963 | 0 | 0.03606667 | 0.59037037 | 0.10551852 | 0.31614815 | 0.02811111 | 0.067 |

Example 4—Use of the Average of Several Thiols as Model Thiol

In Example 1 rate enhancements were calculated relative to the control thiol, glutathione. The data from Example 3 show that an average of several different thiols may be used as a control.

As an example, the rate constant for ligand candidate EL1157 in reaction with all the Cdk2 constructs (except Cdk(WT)) were averaged and then compared to the rate constant with Cdk2(WT).

TABLE 6

Rate constants for ligand candidate EL1157 in reaction with various Cdk2 constructs compared to the rate constant in reaction with Cdk2(WT)

| Mutant | Rate constant |
| --- | --- |
| k(Cdk2(F80C)) | 0.0393 h$^{-1}$ |
| k(Cdk2(H71C)) | 0.0261 h$^{-1}$ |
| k(Cdk2(S276C)) | 0.0704 h$^{-1}$ |
| k(Cdk2(N272C)) | 0.0029 h$^{-1}$ |
| k(Cdk2(T182C)) | 0.1572 h$^{-1}$ |
| k(Cdk2(R122C)) | 0.0048 h$^{-1}$ |
| k(Cdk2(S181C)) | 0.0138 h$^{-1}$ |
| k(average) | 0.0449 h$^{-1}$ |
| k(Cdk2(WT)) | 0.2006 h$^{-1}$ |
| k(Cdk2(WT))/k(average) | 4.46 |

This value of rate enhancement using an average of multiple proteins as a control thiol gives a measure of selectivity of hit ligands for the target protein.

Example 5

As an example of the determination of $k_2$ and $K_d$ for one of the hit ligands (CA37) identified against Cdk2(C177A, F80C), the observed rate constant was calculated at ligand candidate concentrations of 2, 1, 0.5, 0.35, 0.2, 0.1, 0.05 and 0.02 mM, (see Table 7 below). Rate constants were calculated as described in the methodology section of Examples 1 and 2.

TABLE 7

Rate constants for various concentrations of CA37 binding to Cdk2 (C177A, F80C)

| [CA37] (mM) | $k_{obs}$ (min$^{-1}$) |
| --- | --- |
| 2 | 0.005626 |
| 1 | 0.004177 |
| 0.5 | 0.002372 |
| 0.35 | 0.002029 |
| 0.2 | 0.001313 |
| 0.1 | 0.0006704 |
| 0.05 | 0.000271 |
| 0.02 | 0.00007107 |

Fitting the hyperbolic equation to this data (FIG. 9) gives $K_d$=1.2 mM, $k_2$=0.009427 min$^{-1}$.

Example 6—Validation of Hit Ligand

Mass spectrometry and X-ray crystallography were used to validate the binding of a hit ligand identified by the present method.

From the screen of Cdk2(F80C, C177A), we identified EL1071 as a hit molecule (rate enhancement relative to GSH=60.5). The labelling was cross-validated by intact protein mass spectrometry (which showed that after 2 hours of incubation Cdk2(F80C, C177A) was completely mono-modified by EL1071 (In this figure Cdk2(AS)=Cdk2(F80C, C177A), 1=EL1071)—see FIG. 10(a).

The resulting complex was then digested with trypsin and the resulting peptides sequenced by tandem mass spectrometry which confirmed the site of modification as F80C (FIG. 10(b)).

A kinase assay was also performed which showed that Cdk2(F80C, C177A) has comparable activity to Cdk2(WT) and that EL1071 completely inhibited Cdk2(F80C, C177A). Again, 1-Cdk2 refers to Cdk2(F80C, C177A) labelled with EL1071 (FIG. 10(c)). Finally, the EL1071-Cdk2(F80C, C177A) complex was crystallized and the structure determined by X-ray crystallography (FIG. 11). This confirms that the ligand binds to the cysteine residue at F80C and blocks the protein's active site leading to the observed inhibition.

REFERENCES

1. Erlanson, D. A, Wells, J. A. and Braisted, A. C. 2004. Tethering: Fragment-Based Drug Discovery. *Annu. Rev. Biophys. Biomol. Struct.*, 33, 199-223.
2. WO 2005/034840
3. US 2002/0022233
4. Kathman, S. G., Xu, Z. and Statsyuk, A. V. 2014. A Fragment-Based Method to Discover Irreversible Covalent Inhibitors of Cysteine Proteases. *J. Med. Chem.*, 57, 4969-4974.
5. Nonoo, R. H, Armstrong, A. and Mann, D. J. 2012. Kinetic Template-Guided Tethering of Fragments. *Chem. Med. Chem.*, 7, 2082-2086.
6. Allen, C. E.; Curran, P. R.; Brearley, A. S.; Boissel, V.; Sviridenko, L.; Press, N.J.; Stonehouse, J. P.; Armstrong, A. 2015. Efficient and Facile Synthesis of Acrylamide Libraries for Protein-Guided Tethering. *Org. Lett.*, 17, 458-460
7. Hong, V.; Kislukhin, A. A.; Finn, M. G. 2009. Thiol-Selective Fluorogenic Probes for Labeling and Release *J. Am. Chem. Soc.*, 2009, 131 (29), 9986-9994
8. Yi L, Li H, Sun L, Liu L, Zhang C, Xi Z 2009. A highly sensitive fluorescence probe for fast thiol-quantification assay of glutathione reductase *Angew Chem Int Ed Engl.* 48(22):4034-7.
9. Chen, X.; Zhou, Y.; Peng, X. and Juyoung, Y., 2010. Fluorescent and colorimetric probes for detection of thiols. *Chem. Soc. Rev.*, 39, 2120-2135
10. Alzahrani, E.; Welham, K. 2014. Fabrication of a TCEP-immobilised monolithic silica microchip for reduction of disulphide bonds in proteins *Anal. Methods*, 6, 558-568

All of the references set out above are herein incorporated by reference.

The invention claimed is:

1. A method of measuring the rate of reaction between a target protein and a ligand candidate, wherein the ligand candidate is a small molecule having a molecular weight of 900 Da or less, the method comprising the steps of:
   a) providing a target protein comprising an endogenous surface-exposed cysteine residue near the ligand binding site of the target protein, wherein the cysteine residue comprises a free thiol group;
   b) initiating the reaction by contacting the target protein from step a) with the ligand candidate, wherein the ligand candidate comprises a functional group which is capable of forming an irreversible covalent bond with said free thiol group thereby forming a reaction mixture in which
   an irreversible covalent bond is formed between the thiol group of the target protein and the functional group of the ligand candidate, thereby forming a target protein-ligand conjugate;
   c) contacting the reaction mixture or an aliquot thereof with a thiol quantification reagent at a defined time point during the reaction, wherein the thiol quantification reagent is capable of bonding to free thiol groups to form a quantification conjugate which provides the reaction mixture or aliquot thereof with a biophysical property assessable by a biophysical method;
   d) measuring the biophysical property of the reaction mixture or aliquot thereof; and
   e) calculating the rate of reaction between the target protein and the ligand candidate using the measured biophysical property of the reaction mixture or aliquot thereof.

2. The method of claim 1, wherein step c) comprises contacting an aliquot of the reaction mixture with the thiol quantification reagent, wherein steps c) and d) are repeated one or more further times, and wherein, during each repetition, step c) is carried out at one or more further, different time points during the reaction.

3. The method of claim 1, wherein step c) comprises contacting the entire reaction mixture or a substantial proportion thereof with the thiol quantification reagent, wherein steps a) to d) are repeated one or more further times, and wherein, during each repetition, step c) is carried out at one or more further, different time points during the reaction.

4. The method of claim 2, wherein step e) comprises calculating a rate constant for the formation of the target protein-ligand conjugate.

5. The method of claim 1, wherein step c) is carried out at a single time point during the reaction and wherein step e) comprises calculating the conversion of the target protein to the target protein-ligand candidate at that time point; and optionally, further comprising calculating an approximation of a rate constant for the formation of the target protein-ligand conjugate.

6. The method of claim 1 wherein the target protein is selected from the group consisting of a nucleoprotein, a glycopeptide and a phosphoprotein.

7. The method of claim 1 wherein the ligand candidate is fragment.

8. The method of claim 7 wherein the ligand candidate is a drug-like fragment.

9. The method of claim 1 wherein the functional group is an electrophile.

10. The method of claim 9 wherein the electrophile is selected from the group consisting of acrylamide, acrylate, α,β-unsaturated ketone, vinyl sulfonamides, vinylsulfone, vinylsulfonate, α-halogenated carbonyl derivatives such as α-chloroketones and α-chloroacetamides, epoxides, nitrile derivatives, $S_NAr$ substrates and substituted derivatives thereof; or
   wherein the electrophile is a Michael acceptor.

11. The method of claim 1 wherein the thiol quantification reagent is a thiol-reactive dye.

12. The method of claim 1 wherein the target protein and the ligand candidate are contacted in the presence of a reducing agent, optionally, wherein the reducing agent is immobilised.

13. The method of claim 1, further comprising the steps of:
   f) repeating steps e) to using a model thiol instead of the target protein, to calculate the rate of reaction between the model thiol and the ligand candidate, using the same ligand candidate; and
   g) calculating the rate enhancement for the ligand candidate by comparing the rate of reaction between the target protein and the ligand candidate against the rate of reaction between the model thiol and the ligand candidate.

14. The method of claim 13 wherein the model thiol is glutathione, and optionally further comprising the step of:
   h) determining whether the rate enhancement for the ligand candidate is above a chosen threshold level, wherein a ligand candidate with a rate enhancement above this threshold level is classified as a hit ligand.

15. The method of claim 14, further comprising the step of:
   i) repeating steps a) to h) with one or more further ligand candidates.

16. The method of claim 14 wherein the ligand candidates comprise a library of ligand candidates.

17. The method of claim 14, further comprising the step of:
  j) developing a hit ligand into a drug or other inhibitor.

18. The method of claim 17, wherein either:
  a) the hit ligand is developed into an irreversible covalent inhibitor; or
  b) the hit ligand is modified into a non-covalent analogue and developed into a reversible inhibitor.

19. The method of claim 17, wherein the hit ligand is modified into a non-covalent analogue and developed into a reversible inhibitor.

20. A method of measuring the dissociation constant between a target protein and a ligand candidate, wherein the ligand candidate is a small molecule having a molecular weight of 900 Da or less, the method comprising the steps of:
  a) providing a target protein comprising an endogenous, surface-exposed cysteine residue, near the ligand binding site of the target protein wherein the cysteine residue comprises a free thiol group;
  b) initiating the reaction by contacting the target protein from step a) with a ligand candidate, wherein the ligand candidate comprises a functional group which is capable of forming an irreversible covalent bond with said free thiol group thereby forming a reaction mixture in which an irreversible covalent bond between the thiol group of the target protein and the functional group of the ligand candidate is formed, thereby forming a target protein-ligand conjugate;
  c) contacting the reaction mixture or an aliquot thereof with a thiol quantification reagent at a defined time point during the reaction, wherein the thiol quantification reagent is capable of bonding to free thiol groups to form a quantification conjugate which provides the reaction mixture or aliquot thereof with a biophysical property assessable by a biophysical method;
  d) measuring the biophysical property of the reaction mixture or aliquot thereof;
  e) calculating the rate of reaction between the target protein and the ligand candidate using the measured biophysical property of the reaction mixture or aliquot thereof;
  f) repeating steps a) to f) with multiple different concentrations of the ligand candidate; and
  g) calculating the dissociation constant between the target protein and the ligand candidate.

21. The method of claim 6, wherein the target protein is an enzyme.

22. The method of claim 21, wherein the enzyme is a cyclin-dependent kinase 2.

* * * * *